US009534020B2

(12) United States Patent
Cardozo et al.

(10) Patent No.: US 9,534,020 B2
(45) Date of Patent: Jan. 3, 2017

(54) IMMUNOGENIC POLYPEPTIDES COMPRISING A MODIFIED LOOP PEPTIDE PRESENTING THE HIV-1 GP120 3074 MAB EPITOPE AND SCAFFOLD PROTEINS CONTAINING SAID PEPTIDE

(75) Inventors: Timothy Cardozo, New York, NY (US); Xiang-peng Kong, New York, NY (US); Susan Zolla-Pazner, New York, NY (US); Shan Lu, Franklin, MA (US); Shixia Wang, Northborough, MA (US); Maxim Totrov, San Diego, CA (US)

(73) Assignees: New York University, New York, NY (US); University of Massachusetts, Boston, MA (US); Molsoft LLC, San Diego, CA (US)

( * ) Notice: Subject to any disclaimer, the term of this patent is extended or adjusted under 35 U.S.C. 154(b) by 118 days.

(21) Appl. No.: 13/876,918

(22) PCT Filed: Sep. 28, 2011

(86) PCT No.: PCT/US2011/053686
§ 371 (c)(1),
(2), (4) Date: Jun. 25, 2013

(87) PCT Pub. No.: WO2012/050893
PCT Pub. Date: Apr. 19, 2012

(65) Prior Publication Data
US 2013/0287804 A1 Oct. 31, 2013

Related U.S. Application Data

(60) Provisional application No. 61/387,842, filed on Sep. 29, 2010.

(51) Int. Cl.
| C07K 14/005 | (2006.01) |
| C07K 7/08 | (2006.01) |
| A61K 39/21 | (2006.01) |
| C07K 14/00 | (2006.01) |
| C07K 14/245 | (2006.01) |
| C07K 14/28 | (2006.01) |
| A61K 39/12 | (2006.01) |
| A61K 39/00 | (2006.01) |

(52) U.S. Cl.
CPC ............ *C07K 14/001* (2013.01); *A61K 39/12* (2013.01); *A61K 39/21* (2013.01); *C07K 7/08* (2013.01); *C07K 14/005* (2013.01); *C07K 14/245* (2013.01); *C07K 14/28* (2013.01); *A61K 2039/53* (2013.01); *A61K 2039/55555* (2013.01); *A61K 2039/6037* (2013.01); *C12N 2740/16034* (2013.01)

(58) Field of Classification Search
CPC .......... C07K 14/005; C07K 7/08; A61K 39/21
See application file for complete search history.

(56) References Cited

U.S. PATENT DOCUMENTS

2008/0206264 A1 8/2008 Anglister et al.
2009/0098144 A1 4/2009 Zolla-Pazner et al.

FOREIGN PATENT DOCUMENTS

WO 2008/005929 A2 1/2008

OTHER PUBLICATIONS

Alexander, H., et al., Apr. 1992, Altering the antigenicity of proteins, Proc. Natl. Acad. Sci. USA 89:3352-3356.*
Watkins, B. A., et al., Dec. 1996, Resistance of human immunodeficiency virus type 1 to neutralization by natural antisera occurs through single amino acid substitutions that cause changes in antibody binding at multiple sites, J. Virol. 70(12):8431-8437.*
Ruth, N., et al., 2008, Creating hybrid proteins by insertion of exogenous peptides into permissive sites of class A beta-lactamase, FEBS J. 275:5150-5160.*
Chakraborty, K., et al., 2006, Design of immunogens that present the crown of the HIV-1 V3 loop in a conformation competent to generate 447-52D-like antibodies, Biochem. J. 399:483-491.*
Hong, Y.-R., et al., 1996, Bacteriophage T4 expression-packaging processing vector that encapsidates HIV-type 1 gp120-V3 fusion protein inside the head, Kaohsiung J. Med. Sci. 12:381-387.*
Cook, J., and B. H. Barber, 1997, Recombinant antibodies with conformationally constrained HIV type 1 epitope inserts elicit glycoprotein 160-specific antibody responses in vivo, AIDS Res. Human Retrovir. 13(6):449-460.*
Agarwal et al., "Quantitative Assessment of Masking of Neutralization Epitopes in HIV-1," Vaccine 29:6736-6741 (2011).
Burke et al., "Structural Basis of the Cross-Reactivity of Genetically Related Human Anti-HIV-1 mAbs: Implications for Design of V3-Based Immunogens," Structure 17:1538-1546 (2009).
Jiang et al., "Conserved structural elements in the V3 crown of HIV-1 gp120," Nature Structural & Molecular Biology 17(8):955-961 (2010).
Shmelkov et al., "Indirect Detection of an Epitope-Specific Response to HIV-1 gp120 Immunization in Human Subjects," PLoS ONE 6(11)(e27279):1-5 (2011).

(Continued)

*Primary Examiner* — Jeffrey Parkin
(74) *Attorney, Agent, or Firm* — LeClairRyan, a Professional Corporation

(57) ABSTRACT

The present invention is directed to a recombinant immunogenic polypeptide. The polypeptide includes a loop peptide inserted into an immunogenic scaffold protein. The loop polypeptide has an amino acid sequence which presents the 3074 mAb- or the 2219/2557 mAb-targeted epitope of the HIV gp120 protein and not other known epitopes of the HIV gp120 protein. When used as an immunogen, the polypeptide induces an antibody response which neutralizes heterologous HIV-1 viruses in a pattern similar to that observed for the 3074 mAb- or the 2219/2557 mAb-targeted epitope, respectively. Pharmaceutical compositions containing the immunogenic polypeptide as well as methods of making and using it are also disclosed.

12 Claims, 8 Drawing Sheets

(56) References Cited

OTHER PUBLICATIONS

Stanfield et al., "Crystal Structures of Human Immunodeficiency Virus Type 1 (HIV-1) Neutralizing Antibody 2219 in Complex With Three Different V3 Peptides Reveal a New Binding Mode for HIV-1 Cross-Reactivity," J. Virology 80 (12):6093-6105 (2006).

Swetnam et al., "Comparative Magnitude of Cross-Strain Conservation of HIV Variable Loop Neutralization Epitopes," PLoS ONE 5(12)(e15994):1-9 (2010).

Zolla-Pazner et al., "Cross-Clade HIV-1 Neutralizing Antibodies Induced With V3-Scaffold Protein Immunogens Following Priming With gp120 DNA," J. Virology 85(19):9887-9898 (2011).

PCT International Search Report and Written Opinion for corresponding PCT International Application No. PCT/US2011/053686 (mailed Apr. 18, 2012).

Wu et al., "Rational Design of Envelope Identifies Broadly Neutralizing Human Monoclonal Antibodies to HIV-1," Science 329(5993):856-861 (2010).

Zhou et al., "Structural Basis for Broad and Potent Neutralization of HIV-1 by Antibody VRC01," Science 329 (5993):811-817 (2010).

Swetnam et al., "P20-09. Worldwide Epitope Prevalence of Crystallographically Resolved Anti-V3 Antibodies," Retrovirology 6(Suppl 3):P379 (2009).

Hioe et al., "Anti-V3 Monoclonal Antibodies Display Broad Neutralizing Activities Against Multiple HIV-1 Subtypes," PLos ONE 5(4)(e10254):1-14.

* cited by examiner

2219/2557 DESIGNED ANTIGEN: RKSINFGPGQTFYA (SEQ ID NO:3)
- ELIMINATES 3074
- ELIMINATES 447-52D
- ELIMINATES CHARGED RESIDUE IN TYPE SPECIFICITY AREA
- PROMOTES 2219/2557

3074 DESIGNED ANTIGEN: TESINIGPGQTFYA (SEQ ID NO:1)
- ELIMINATES 2219/2557
- ELIMINATES 447-52D
- ELIMINATES CHARGED RESIDUE IN TYPE SPECIFICITY ZONE
- PROMOTES 3074

*FIG. 1*

| MAB | V3(2219)-CTB | V3(3074)-CTB |
|---|---|---|
| 257-D | 3.3 | 0.6 |
| 268-D | 0.3 | 0.6 |
| 311-11D | 0.1 | 0.4 |
| 386-D | 0.3 | 0.6 |
| 391/95-D | 1.8 | 0.6 |
| 412-D | 0.2 | 0.5 |
| 418-D | 0.4 | 0.5 |
| 419-D | 4.4 | 3.9 |
| 447-52D | 4.1 | 0.6 |
| 453-D | 0.2 | 0.6 |
| 504-D | 0.7 | 0.5 |
| 537-D | 0.2 | 0.6 |
| 694/98-D | 0.4 | 0.6 |
| 782-D | 2.3 | 0.5 |
| 838-D | 3.7 | 0.4 |
| 908-D | 3.9 | 0.4 |
| 1006-15D | 3.7 | 0.5 |
| 1027-15D | 3.5 | 0.4 |
| 1108-D | 0.8 | 0.6 |
| 1334 | 4.3 | 0.6 |
| 2182 | 0.3 | 0.6 |
| 2191 | 4.2 | 0.5 |
| 2219 | 4.2 | 0.5 |
| 2412 | 1.3 | 0.6 |
| 2442 | 2.1 | 0.4 |
| 2456 | 3.6 | 0.4 |
| 2483 | 3.7 | 0.4 |
| 2424 | 0.3 | 0.1 |
| 2557 | 3.8 | 0.5 |
| 2558 | 3.9 | 0.5 |
| 2601 | 4.2 | 0.4 |
| 3019A | 4.2 | 0.5 |
| 3074 | 4.2 | 3.9 |
| 1324 | 3.9 | 4.1 |
| 3694 | 3.9 | 0.9 |
| 3697 | 3.7 | 0.5 |
| 3791 | 3.7 | 0.3 |
| 3792 | 3.9 | 0.2 |
| 3869 | 3.6 | 0.3 |
| 3881 | 3.8 | 4.1 |
| 3904 | 3.9 | 4.4 |
| 3906 | 4.3 | 0.3 |
| 4022 | 4.3 | 0.4 |
| 4025 | 4.4 | 0.5 |
| 4085 | 3.2 | 0.5 |
| 4121 | 3.8 | 0.3 |
| 4139 | 4.0 | 3.9 |
| 4210 | 3.7 | 0.3 |
| 3527 | NT | 3.9 |
| 1418 | 0.1 | 0.1 |

*FIG. 2A*

| MAB | V3(2219)-SF162 | V3(3074)-SF162 |
|---|---|---|
| 257-D | n | n |
| 268-D | n | n |
| 311-11D | n | n |
| 386-D | n | n |
| 391/95-D | n | n |
| 412-D | n | n |
| 418-D | n | n |
| 419-D | n | n |
| 447-52D | RESISTANT | RESISTANT |
| 453-D | n | n |
| 504-D | n | n |
| 537-D | n | n |
| 694/98-D | n | n |
| 782-D | n | n |
| 838-D | n | n |
| 908-D | n | n |
| 1006-15D | n | n |
| 1027-15D | n | n |
| 1108-D | n | n |
| 1334 | n | n |
| 2182 | RESISTANT | RESISTANT |
| 2191 | RESISTANT | RESISTANT |
| 2219 | SENSITIVE | RESISTANT |
| 2412 | RESISTANT | RESISTANT |
| 2442 | RESISTANT | RESISTANT |
| 2456 | RESISTANT | RESISTANT |
| 2483 | n | n |
| 2424 | n | n |
| 2557 | SENSITIVE | RESISTANT |
| 2558 | SENSITIVE | RESISTANT |
| 2601 | RESISTANT | RESISTANT |
| 3019A | RESISTANT | RESISTANT |
| 3074 | RESISTANT | SENSITIVE |
| 1324 | n | n |
| 3694 | RESISTANT | RESISTANT |
| 3697 | RESISTANT | RESISTANT |
| 3791 | RESISTANT | RESISTANT |
| 3792 | RESISTANT | RESISTANT |
| 3869 | n | n |
| 3881 | n | n |
| 3904 | n | n |
| 3906 | n | n |
| 4022 | n | n |
| 4025 | n | n |
| 4085 | n | n |
| 4121 | n | n |
| 4139 | n | n |
| 4210 | n | n |
| 3527 | n | n |
| 1418 | n | n |

*FIG. 2B*

NYU VII - SERUM GROUPS
NEUTRALIZATION OF CHIMERIC psV BEARING SPECIFIC EPITOPES

■ CTB-V3-3074 (GROUP 2)
□ CTB-V3-2219 (GROUP 1)
— CTB-V3-B (GROUP 3)

Non-2219, 3074 Abs INDUCED BY V3-b (447D)

EPITOPES:
- −3074, −2219
- −3074, +2219 / −2219, +3074
- +3074, +2219 (p1531)

NT 50 OF POOLED RABBIT SERA (1/DILUTION)

FIG. 3

| CATEGORY | SUBTYPE | VIRUS ID | ANTI-V3 mAbs | | | | | | | | CONTROL |
|---|---|---|---|---|---|---|---|---|---|---|---|
| | | | 2191 | 2219 | 2557 | 2558 | 3074 | 3869 | 447 | 1418 |
| TIER 2 | C | Du156.12 | >50 | >50 | >50 | >50 | >50 | >50 | >50 | >50 |
| | C | Du172.17 | >50 | >50 | >50 | >50 | >50 | >50 | >50 | >50 |
| | C | Du422.1 | >50 | >50 | >50 | >50 | >50 | >50 | >50 | >50 |
| | C | ZM197M.PB7 | >50 | >50 | >50 | >50 | >50 | >50 | >50 | >50 |
| | C | ZM214M.PL15 | >50 | >50 | >50 | >50 | >50 | >50 | >50 | >50 |
| | C | ZM233M.PB6 | 41.70 | >50 | 48.54 | 46.95 | 40.78 | 37.78 | >50 | >50 |
| | C | ZM249M.PL1 | >50 | >50 | >50 | >50 | >50 | >50 | >50 | >50 |
| | C | ZM53M.PB12 | >50 | >50 | >50 | >50 | >50 | >50 | >50 | >50 |
| | C | ZM109F.PB4 | >50 | >50 | 27.04 | 23.77 | 7.33 | 15.02 | >50 | >50 |
| | C | ZM135M.PL10a | >50 | >50 | >50 | >50 | >50 | >50 | >50 | >50 |
| | C | CAP45.2.00.G3 | >50 | >50 | >50 | >50 | >50 | >50 | >50 | >50 |
| | C | CAP210.2.00.E8 | >50 | >50 | >50 | >50 | 41.48 | >50 | >50 | >50 |

*To / From FIG. 4B*

FIG. 4A

| DNA | PROTEIN | RABBITS# | p1531 B | p782 SF162wt | p1534 F | p1520 A/E | p1522 AI | p1441 A/G | p1530 H | p1636 C | p1515 C(+N GLYCAN) |
|---|---|---|---|---|---|---|---|---|---|---|---|
| IC 50 (SERUM DILUTION) | | | | | | | | | | | |
| gp120. C1.opt(Cq) | V3/2219-CTB | 106 | 72,889 | 3,905 | 2,793 | 4,864 | 2,923 | 2,924 | 83 | 695 | 212 |
| | | 107 | 39,449 | 1,587 | 3,399 | 6,495 | 2,598 | 3,221 | 65 | 732 | 86 |
| | | 108 | 22,768 | 2,857 | 2,252 | 2,542 | 2,070 | 2,735 | 45 | 488 | 137 |
| | | 109 | 41,135 | 3,217 | 2,670 | 1,739 | 1,525 | 1,427 | 186 | 224 | 164 |
| | | 110 | 4,587 | 1,098 | 1,669 | 315 | 1,460 | 999 | 150 | 105 | 129 |
| gp120. C1.opt(Cq) | V3/3074-CTB | 111 | 8,443 | 1,643 | 3,735 | 65,382 | 5,084 | 2,962 | 25 | 930 | 1,122 |
| | | 112 | 26,665 | 1,578 | 8,362 | 1,694 | 3,098 | 1,032 | 174 | 597 | 250 |
| | | 113 | 3,071 | 90 | 5,287 | 7,489 | 2,017 | 2,502 | 35 | 207 | 232 |
| | | 114 | 205 | <50 | 80,192 | 112,600 | 31,476 | 48,185 | 1,884 | 7,321 | 2,264 |
| | | 115 | 3,618 | 356 | 2,341 | 13,043 | 1,041 | 2,139 | 112 | 294 | 557 |
| gp120. C1.opt(Cq) | V3/B-CTB | 116 | 26,153 | 3,220 | 3,291 | 9,977 | 1,420 | 2,659 | 288 | 510 | 215 |
| | | 117 | 22,463 | 3,038 | 2,743 | 2,191 | 1,288 | 2,124 | 192 | 247 | 136 |
| | | 118 | 9,090 | 550 | 1,375 | 449 | 498 | 485 | 67 | 117 | 45 |
| | | 119 | 16,002 | 1,177 | 1,720 | 999 | 1,137 | 1,318 | 15 | 260 | 147 |
| | | 120 | 33,691 | 3,674 | 3,969 | 1,039 | 1,822 | 1,929 | 163 | 201 | 157 |
| gp120. C1.opt(Cq) | V3/H-CTB | 121 | 5,736 | 755 | 2,000 | 450 | 590 | 247 | 72 | 45 | 45 |
| | | 122 | 4,446 | 759 | 541 | 525 | 290 | 358 | 53 | 74 | 50 |
| | | 123 | 19,215 | 1,245 | 2,704 | 1,971 | 1,100 | 1,009 | 374 | 235 | 56 |
| | | 124 | 10,151 | 3,175 | 1,087 | 2,298 | 480 | 324 | 70 | 76 | 51 |
| | | 125 | 3,040 | 980 | 424 | 371 | 605 | 450 | 30 | 79 | 20 |
| gp120. C1.opt(Cq) | V3/B-CTB + V3/H-CTB | 126 | 1,300,000 | 3,771 | 45,007 | 39,595 | 9,142 | 36,500 | 745 | 2,872 | 1,703 |
| | | 127 | 92,851 | 13,693 | 7,318 | 1,833 | 2,950 | 9,350 | 348 | 469 | 190 |
| | | 128 | 2,300,000 | 35,235 | 105,000 | 113,584 | 24,199 | 50,214 | 4,053 | 5,153 | 3,718 |
| | | 129 | 43,316 | 14,642 | 7,991 | 21,186 | 3,332 | 12,398 | 215 | 550 | 1,823 |
| | | 130 | 10,159 | 1,159 | 849 | 837 | 846 | 579 | 225 | 158 | 108 |

GEOMEAN 50% AND 90% NEUTRALIZING TITERS FOR RABBIT SERA POOLS FROM NYU-VII VERSUS SELECTED V3 CHIMERIC PSEUDOVIRUSES
DATA ARE CALCULATED FROM 2-3 EXPERIMENTS

| I. NT 50 | | | | | | | | | |
|---|---|---|---|---|---|---|---|---|---|
| DNA | BOOST PROTEIN | POOL RABBITS# | p1531 CONSENSUS B | p1788 B-K10E | p1767 B-I14M | p1558 B-R18Q | p1915 B-K10E/114M | p1917 B-K10E/R18Q | p1916 B-114M/R18Q |
| gp120. C1.opt(Cq) | V3/2219-CTB | 106-110 | 43435 | 5048 | 17114 | 3776 | 807 | 1671 | 7499 |
| gp120. C1.opt(Cq) | V3/3074-CTB | 111-115 | 24733 | 4500 | 4390 | 19945 | 53 | 20164 | 29651 |
| gp120. C1.opt(Cq) | V3/B-CTB | 116-120 | 48785 | 8132 | 16280 | 4285 | 4516 | 3800 | 8910 |
| gp120. C1.opt(Cq) | V3/H-CTB | 121-125 | 13623 | 3507 | 8955 | 1300 | 771 | 1600 | 6413 |
| gp120. C1.opt(Cq) | V3/B+H-CTB | 126-130 | 205428 | 37678 | 117192 | 21374 | 7097 | 27827 | 47819 |

*FIG. 5*

FINAL 4/23/09

GMT50 VALUES FOR NYU7 SERA
ALL <10 VALUES REMOVED FROM THIS TABLE

| | | CLADE B | | | CLADE A | | | | CLADE A/G | | | | CLADE C | | |
|---|---|---|---|---|---|---|---|---|---|---|---|---|---|---|---|
| | BX08 | BZ167 | CA5 | NYU3738 | VI191 | VI313 | CA1 | DJ263 | NYU6525(2) | NYU1295) | 97ZA009 | 98CN006 | 92BR025 | 93MW965 | 93MW960 |
| C.1 opt/ V3 2219-CTB LONG | 60 | 268 | | | | 17 | | 1171 | | | | | | | |
| C.1 opt/ V3 3074-CTB LONG | 29 | 139 | | | | | | 1606 | | | | | | | |
| C.1 opt/ V3B-CTB LONG | 63 | 753 | 96 | | | 26 | | 608 | | | | | | | |
| C.1 opt/ V3H-CTB LONG | 20 | 261 | | | | 47 | | 302 | | | | | | | |
| C.1 opt/ V3B+V3H CTB LONG | 160 | 393 | 79 | 20 | | 35 | 51 | 1918 | | | | | | | |

FIG. 6

IMMUNOGENIC POLYPEPTIDES COMPRISING A MODIFIED LOOP PEPTIDE PRESENTING THE HIV-1 GP120 3074 MAB EPITOPE AND SCAFFOLD PROTEINS CONTAINING SAID PEPTIDE

This application is a national stage application under 35 U.S.C. §371 of PCT Application No. PCT/US2011/053686, filed Sep. 28, 2011, which claims the priority benefit of U.S. Provisional Patent Application Ser. No. 61/387,842, filed Sep. 29, 2010, both of which are hereby incorporated by reference in their entirety.

FIELD OF THE INVENTION

The present invention relates generally to immunogenic polypeptides having an immunogenic scaffold protein and a loop peptide, presenting a 3074- or 2219/2557-monoclonal antibody-targeted epitope, which is present in the HIV GP120 protein.

BACKGROUND OF THE INVENTION

Effective vaccination against HIV remains the only viable means to stop the spread of the AIDS pandemic. However, numerous attempts to elicit protective immunity to HIV have been unsuccessful. Prior efforts to elicit protective immunity have at best achieved protection in animals to the same strain that is inoculated.

A wide variety of monoclonal antibodies have been isolated from the serum of HIV infected human subjects, and these antibodies display a spectrum of activities from (a) binding just one strain of HIV-1, but not neutralizing it, to (b) binding more than one strain of HIV-1 but not neutralizing them, to (c) neutralizing just one strain of HIV-1 and either binding only that strain or binding many strains, to (d) neutralizing many strains of HIV-1 (a "broadly neutralizing" antibody). These activities suggest that these antibodies, should they be present in the serum of a human who has never been infected with the HIV virus, would protect that human from infection with the HIV-1 virus should the human be exposed to the HIV-1 virus.

The majority of antibodies generated against the HIV envelope glycoprotein gp120 are not neutralizing, either because their binding does not prevent fusion of HIV to its target cells or because the epitopes they recognize are inaccessible to the antibody. Therefore, focusing the immune response to regions of gp120 that are known to bind neutralizing antibodies may improve the efficacy of vaccination. With few exceptions, even antibodies with neutralizing activity are only reactive against a limited number of HIV strains, a result of most antibody epitopes being subject to high sequence variability.

The V3 region of the surface envelope glycoprotein of HIV-1 (120), which is the primary vaccine target in HIV-1, has given rise to many of the monoclonal antibodies in all four binding and neutralization categories that have been isolated. The V3 region of gp120, while generally variable, possesses conserved features that allow broad neutralization by certain antibodies such as the human monoclonal antibody (mAb) 447-52D (also referred to herein as 447-52 and 447). 447-52D recognizes the conserved tip of the V3 loop in a β-turn conformation.

However, most anti-V3 antibodies have narrow neutralization profiles. A specially designed V3-based immunogen that could induce high titers of antibodies with a binding mode and epitope specificity that is similar to that of one or more known broadly neutralizing antibodies (for example, 447-52D) would be expected to be valuable as an HIV vaccine.

Cholera Toxin subunit B ("CTB") and a family of closely related bacterial proteins, such as E. coli enterotoxins, are homopentamers made of relatively small subunits (~100 aa). The protein is highly immunogenic and has been used generally in fusion constructs to enhance immunogenicity of its fusion partner polypeptide or peptide. CTB has been described as a mucosal adjuvant for vaccines, genetically fused the ctxB gene to the psaA gene from *Streptococcus pneumoniae*, a surface protein, a vaccine antigen candidate. Purified CTB-PsaA expressed in *E. coli*, was used for intranasal immunization of mice and induced systemic and mucosal antibodies in serum, saliva, and in nasal and bronchial wash samples.

An important factor for the immunogenic property of CTB and related toxins is their binding to GM1 ganglioside. X-ray structures of CTB revealed that the oligosaccharide binding sites are formed by residues E51, Q56, H57, Q61, W88, N90, and K91. The availability of this structural information allows protein design that avoids or minimizes disruption of the CTB GM1 binding site, thereby preserving the inherent immunogenicity of these polypeptides. When used as a delivery means of a vaccine to mucosal immune systems, CTB cannot tolerate large-protein fusion which impairs pentamerization and lowers affinity for GM1-ganglioside. A new strategy to reduce steric hindrance between CTB-antigen fusion subunits promoted integration of unfused CTB "molecular buffers" into the pentamer unit, leading to more efficient self-assembly into biologically active pentamers. The chimeric protein took on a compact configuration, becoming small enough to be secreted. Affinity-purified proteins administered by a mucosal route induced specific immune responses in mice, a finding that was considered broadly applicable to bacterial enterotoxin-based vaccine design.

Its propensity to induce mucosal immunity is another advantage of CTB as an immunogenic "carrier" that is uncommon, yet is highly desirable for an HIV immunogen or vaccine, because infection commonly occurs via a mucosal route. Furthermore, CTB is not toxic without the concomitant presence of the A subunit (that is part of the native cholera toxin). CTB has been approved as a component of an anti-cholera vaccine for use in humans.

In an attempt to generate an immunogen competent to generate 447-52D-like antibodies, the known epitope of 447-52D was inserted at three different surface loop locations in the small, stable protein *Escherichia coli* thioredoxin (Trx). At one of the three locations (between residues 74 and 75), the insertion was tolerated (i.e., the resulting protein was stable and soluble) and bound 447-52D with an affinity similar to that of intact gp120. Upon immunization, with the V3 peptide-Trx scaffold, anti-V3 antibodies were induced that could compete for 447-52D binding to gp120. These anti-V3 antibodies were said to recognize the same epitope as 447-52D. The 447-52D-lik Abs were estimated to be present at concentrations of 50400 μg/ml of serum and were unable to effect neutralization of HIV-1 strains like JR-FL and BAL but could neutralize the sensitive MN strain. The authors suggested that because of the low accessibility of the V3 loop on primary HIV-1 isolates such as JRFL, it will be difficult to elicit a V3-specific, 447-52D-like antibody response to effectively neutralize such isolates.

It has also been observed that if the HIV-MN V3 epitope is placed in a scaffold, only strain-specific neutralization (of the MN strain) occurs.

An important surrogate end point for using the information represented by these monoclonal antibodies to eventually elicit protective immunity in humans to HIV is the capability to specifically elicit an animal serum antibody response that mimics the behavior of a specific monoclonal antibody. This capability is equally important in general for specifically utilizing similar functionally promising monoclonal antibodies to elicit protective immunity to any infectious human pathogen. A specially designed V3-based immunogen that could induce high titers of antibodies with a binding mode and epitope specificity that is similar to that of one or more known broadly neutralizing antibodies (for example, 3074) is expected to be valuable as an HIV vaccine.

Amino-acid sequence pattern in proteins that have biological significance are termed sequence motifs and usually are a low resolution representation of a stereotypical three-dimensional structural shape in the protein that is of functional or biological significance. Therefore, neutralization epitopes targeted by antibodies, which are stereotypical three-dimensional structural shapes on the molecular surface of pathogenic proteins, can be described by sequence motifs.

However, sequence motifs would not have been utilized by skilled scientists for the purposes of antigen design. First, it would not have been expected that a method to design an antigen presenting a particular epitope by way of one-dimensional sequence motifs would be superior to methods aiming to copy the three-dimensional shape of the epitope. Second, deleting epitopes by point mutations while preserving one desired epitope would not have been thought to be effective because numerous epitopes are always present and which antibodies do and do not arise from a particular protein despite the presence of many epitopes is not known. Third, whether motifs for antibody binding epitopes or motifs for antibody neutralization epitopes are more effective at eliciting specific near-monoclonal antibody responses in serum is not known. Not surprisingly then, the use of sequence motifs for epitopes as immunogen design tools, and as tools to analyze antibody responses in serum resulting from immunogen inoculation in animals and humans has never been described.

The present invention is directed to overcoming these deficiencies in the art.

SUMMARY OF THE INVENTION

One aspect of the present invention is directed to a recombinant immunogenic polypeptide. The polypeptide includes a loop peptide inserted into an immunogenic scaffold protein. The loop polypeptide has an amino acid sequence which presents the 3074 mAb- or the 2219/2557 mAb-targeted epitope of the HIV gp120 protein and not other known epitopes of the HIV gp120 protein. When used as an immunogen, the polypeptide induces an antibody response that neutralizes heterologous HIV-1 viruses in a pattern similar to that observed for the 3074 mAb- or the 2219/2557 mAb-targeted epitope, respectively.

Another aspect of the present invention relates to a method of preparing an immunogenic polypeptide capable of generating an immune response against an antigen of interest. This method includes identifying the known epitopes of the antigen of interest, providing candidate agents in which all but one of the identified known epitopes of the antigen of interest are eliminated, and immunizing a mammal with the candidate agents. Serum from the immunized mammal is recovered, and it is determined if the recovered serum recognizes the antigen of interest. Candidate agents whose serum is recognized by the antigen of interest are identified as immunogenic polypeptides.

As described supra, elicitation of HIV-1 immune sera capable of neutralizing a spectrum of HIV-1 viruses has been a major unaddressed challenge for HIV-1 vaccine design. The present invention represents an innovative solution to this problem by the rational design of an HIV-immunogen mimicking a specific HIV-1 neutralizing monoclonal antibody (mAb) epitope with a concordant mammalian immune serum response. This work, for the first time, bridges the gap between the promising structural immunology on HIV-1 neutralizing human monoclonal antibodies and the "reverse" vaccinology required to deploy the observed antibody properties into an efficacious HIV-1 vaccine.

BRIEF DESCRIPTION OF THE DRAWINGS

FIG. 1 illustrates the method used to design V3 loop sequences to exclusively present specific epitopes. The consensus subtype C V3 loop sequence was modified by point mutations to destroy the epitopes (defined as in Cardozo et al., "Worldwide Distribution of HIV Type 1 Epitopes Recognized by Human Anti-V3 Monoclonal Antibodies," *AIDS Res. Hum. Retroviruses* 25(4): 441-450 (2008) and in Swetman et al., "Worldwide Epitope Prevalence of Crystallographically Resolved Anti-V3 Antibodies," *Retrovirology* 2009, 6(Suppl 3):P379 (2009), which are hereby incorporated by reference in their entirety) for specific mAbs. The two lists describe how specific epitopes were eliminated, for each of two immunogenic polypeptide designed antigens (2219/2557 and 3074), respectively, to produce the designed antigens of SEQ ID NO:1 and SEQ ID NO:3, as shown in FIG. 1. The text of each list corresponds to the amino acid letter being discussed in that design. Each list describes how a modification was made at specific locations of the V3 loop that was hypothesized to attract type specific or narrow/decoy antibody responses for both 2219/2557 and 3074 designed antigens. These amino acids were modified to charged or polar residues to reduce the attraction. Each list, respectively, also describes how the target epitope was preserved in the design, and the text refers to the amino acids in the sequence. The structure of the resulting immunogen is shown at the bottom of the figure with the pentavalent cholera toxin B (CTB) scaffold without inserted designed loops shown and the chimeric CTB-V3 loop immunogen with the inserted designed loop. In reality, five structures form a pentamer like that shown with five valencies of the designed V3 loop for immunization.

FIGS. 2A-B illustrate the binding and neutralization of engineered antigenic V3 loop sequences exclusively presenting epitopes targeted by 2219 [V3(2291)-CTB] or 3074 [V3(3074)-CTB]. FIG. 2A illustrates epitopes targeted by 2219 [V3(2291)-CTB]. The left-most column lists 49 different anti-V3 loop monoclonal antibodies and one anti-parvovirus negative control monoclonal antibody ("1418"). The center column shows the OD values resulting from an ELISA assay measuring the binding of the respective antibody to the V3(2219)-CTB immunogen. Strong binding/high OD values are darkly shaded, OD values with moderate binding are lightly shaded, and OD values with no reactivity are not shaded. The right column shows the results for the V3(3074)-CTB immunogen. 2557 and 2558 monoclonal antibodies are similar to 2219 monoclonal antibody, as determined by the 3D similarity in the crystallographic structures of these mAbs with V3 loop peptides as determined in Jiang et al., "Conserved Structural Elements in the V3 Crown of HIV-1 gp120," *Nat Struct Mol. Biol.* 17(8):

955-61 (2010), which is hereby incorporated by reference in its entirety. V3(3074)-CTB specifically binds to 3074 and a few other mAbs. The crystallographic structures/fine specificity of other mAbs bound is unknown, but are believed to be 3074-like. FIG. 2B illustrates epitopes targeted by 3074 [V3(3074)-CTB]. The left-most column lists 49 different anti-V3 loop monoclonal antibodies and one anti-parvovirus negative control monoclonal antibody ("1418"). The middle column shows the interpreted $IC_{50}$ values resulting from an in vitro neutralization assay measuring the antibody-mediated neutralization of a chimeric SF162 based pseudovirus bearing the V3(2219)-CTB design as its V3 loop crown. For $IC_{50}$ values of less than 1 μg/ml, the virus is labeled as "sensitive" to the mAb. For all other values, the virus is labeled as "resistant" to the mAb. Monoclonal antibodies that were not tested are labeled "n." The pseudovirus bearing the V3(2219)-CTB design is sensitive only to the 2219-like mAb.

FIG. 3 illustrates 50% neutralization ("neut") titer of serum resulting from immunization of rabbits with 2219-based immunogen or 3074-based immunogen. The bottom bars show neutralization of HIV pseudovirus containing the targeted epitopes. The middle bars show neutralization when individual epitope is lacking. The top bars illustrate neutralization when both epitopes are lacking Results show neutralization disappears when the epitope is lacking. The serum antibody response is, therefore, 3074 and 2219 specific, respectively.

FIG. 4A illustrates IC50 of neutralization of a Tier 2 panel of HIV pseudoviruses by the pure 3074 monoclonal Ab.

FIG. 5 illustrates chimeric pseudoviruses in which the same SF162 virus displays V3 loops from the consensus virus of seven different HIV subtypes. The seven subtypes (distributed throughout the world) were tested for neutralization by the serum resulting from immunization with the V3-3074-CTB immunogen the V3-2219-CTB immunogen and control immunogens from other studies. Results show that the antibodies raised in the rabbit serum by immunization with V3-3074-CTB neutralizes the V3 loop of all seven subtypes, which is consistent with the broad occurrence of the epitope targeted by the 3074 mAb. Antibodies raised in rabbit serum by immunization with the V3-2219-CTB immunogen neutralize 6 of the 7 diverse V3 loops. Thus, broadly neutralizing antibodies were raised by these immunogens against epitopes so long as the epitopes are not masked or inaccessible in the virus (SF162 presents any V3 loop with full accessibility).

FIG. 6 illustrates primary HIV isolates, which are the most difficult viruses to neutralize in laboratory tests and here were tested for neutralization by the serum resulting from immunization with the V3-3074-CTB immunogen, the V3-2219-CTB immunogen, and control immunogens from other studies. Results show that antibodies raised in rabbit serum by immunization with V3-3074-CTB neutralizes subtypes from two different subtypes B and A/G, suggesting that the 3074-like antibody response raised in the serum was potent. Antibodies raised in rabbit serum by immunization with the V3-2219-CTB immunogen neutralize primary isolates from three different subtypes: B, A and A/G. Thus, potent broadly neutralizing antibodies were raised by these immunogens against partly inaccessible epitopes in difficult to neutralize primary isolates.

DETAILED DESCRIPTION OF THE INVENTION

Figure 4B:
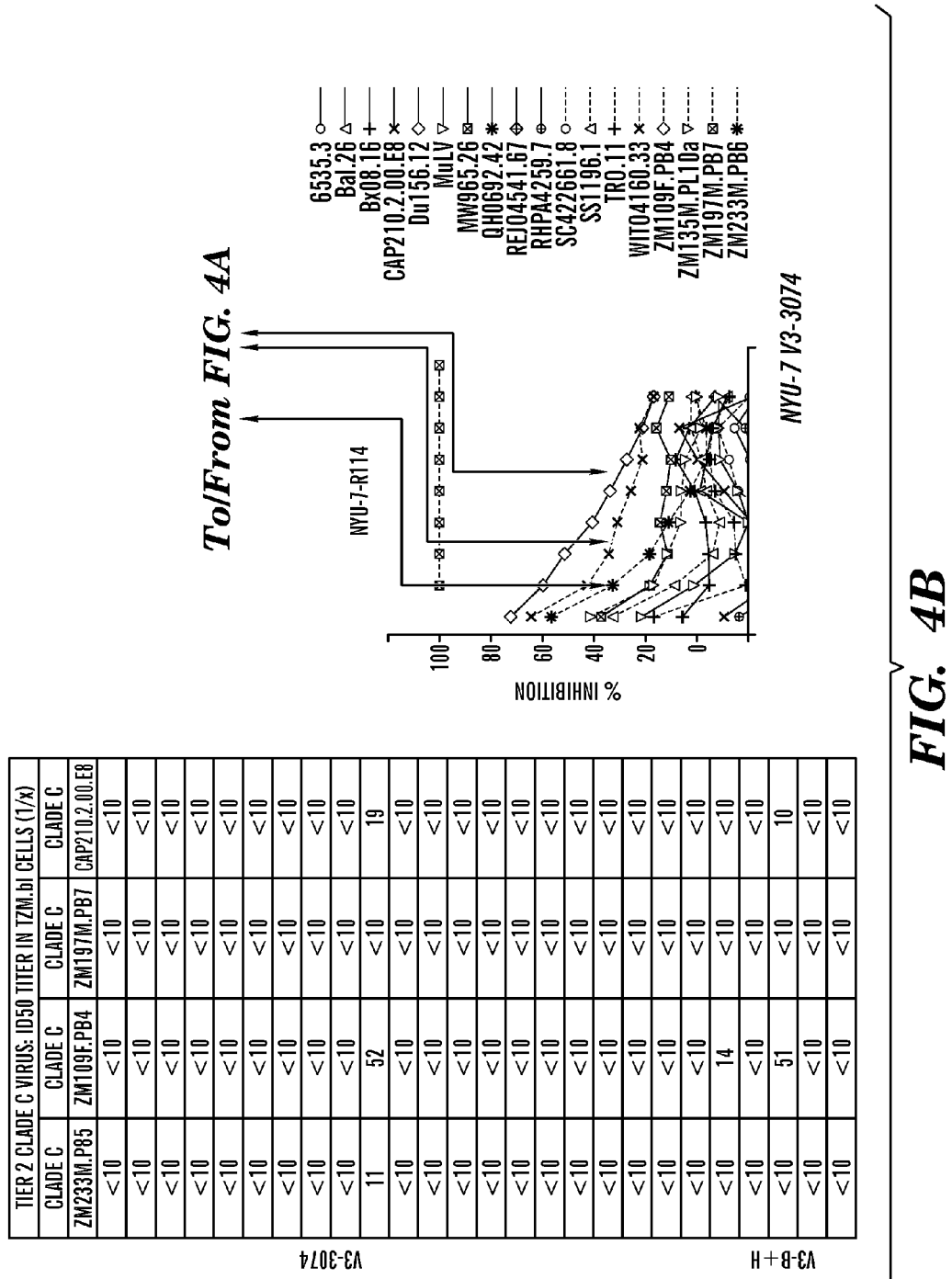
FIG. 4B illustrates neutralization of the same viruses (arrows) by the serum resulting from immunization with the 3074-based immunogen.

The immunogens of the present invention are characterized by specificity for binding to a neutralizing monoclonal antibody and/or inducing a neutralizing immune response against a virus or bacteria. These polypeptides are based on a structurally-defined scaffold having a plurality of discontinuous loops that can be modified to elicit the desired activity. These polypeptides are in some instances referred to as "mimotopes," "peptide mimotopes," "antigenic mimics," "monobodies," or the like.

The antigenic drift of HIV-1 is the most rapid among known infectious pathogens and represents a major obstacle to successful vaccine design. Several broadly HIV-1 neutralizing monoclonal antibodies (nABs) have been isolated that begin to address the HIV-1 antigen variation problem (Wu et al., "Rational Design of Envelope Identifies Broadly Neutralizing Human Monoclonal Antibodies to HIV-1," *Science* 329:859-61 (2010); Zhou et al., "Structural Basis for Broad and Potent Neutralization of HIV-1 by Antibody VRC01," *Science* 329:811-17 (2010); Zolla-Pazner et al., "Structure-Function Relationships of HIV-1 Envelope Sequence-Variable Regions Refocus Vaccine Design," *Nat. Rev. Immunol.* 10(7):527-35 (2010), which are hereby incorporated by reference in their entireties). The promising properties of these antibodies cannot be exploited for HIV-1 vaccine development without the capability of rationally eliciting serum antibody responses in mammalian serum that mimic the specificity of the nAbs.

Recently, sensitive and specific sequence motifs for V3 loop neutralization epitopes (Cardozo et al., "Worldwide Distribution of HIV Type 1 Epitopes Recognized by Human Anti-V3 Monoclonal Antibodies," *AIDS Res Hum Retroviruses* 25(4):441-50 (2009), which is hereby incorporated by reference in its entirety) were derived. The motifs allowed for the search of the HIV-1 database and define by bioinformatics the breadth of occurrence in circulating HIV-1 viruses of several human antibody neutralization epitopes. One antibody, 3074, has a neutralization epitope that is present in more than 80% of HIV-1 viruses infecting patients worldwide (Swetman et al., "Worldwide Epitope Prevalence of Crystallographically Resolved Anti-V3 Antibodies," *Retrovirology* 2009, 6(Suppl 3):P379 (2009), which is hereby incorporated by reference in its entirety). This epitope may, therefore, be viewed as a conserved (antigenically invariant) 3D structure hidden within the immunogenic, but sequence variable V3 loop. The conserved epitope for the 2219 antibody has an epitope "breadth" estimated at 56% of circulating HIV-1 viruses globally, occurring relatively commonly in all subtypes. The neutralization epitopes targeted by these antibodies represent important cross-strain 3D structures that could be valuable targets for serum antibodies elicited by HIV vaccine immunogens.

One aspect of the present invention is directed to a recombinant immunogenic polypeptide. The polypeptide includes a loop peptide inserted into an immunogenic scaffold protein. The loop polypeptide has an amino acid sequence which presents the 3074 mAb- or the 2219/2557 mAb-targeted epitope of the HIV gp120 protein and not other known epitopes of the HIV gp120 protein. When used as an immunogen, the polypeptide induces an antibody response which neutralizes heterologous HIV-1 viruses in a pattern similar to that observed for the 3074 mAb- or the 2219/2557 mAb-targeted epitope, respectively.

In one embodiment, the inserted loop peptide of the recombinant immunogenic polypeptide has an amino acid sequence which presents the 3074 mAb-targeted epitope of the HIV gp120 protein but not the neutralization epitope motifs of the HIV gp120 protein recognized by monoclonal antibodies 2219/2557 and 447-52D. Here, the loop peptide has an amino acid sequence of TESINIGPGQTFYA (SEQ ID NO:1). Alternatively, the polypeptide induces an immune response specifically recognizing the HIV viral epitope targeted by human monoclonal antibody 3074. The immunogenic polypeptide can comprise the amino acid sequence of TPQNITDLCA EYHNTQIHTL NDKIFSYTES LAGKREMAII TFCTRPSNNT TESINIGPGQ TFYATGEIIG DIRQAHCATF QVEVPGSQHI DSQKKAIERM KDTLRIAYLT EAKVEKLCVW NNKTPRAIAA ISMAN (SEQ ID NO:2).

In yet another embodiment, the inserted loop peptide of the recombinant immunogenic polypeptide has an amino acid sequence which presents the 2219/2557 mAb targeted epitope of the HIV gp120 protein but not the neutralization epitope motifs of the HIV gp120 protein recognized by monoclonal antibodies 3074 and 447-52D. Here, the loop peptide has the amino acid sequence comprising RKSINFGPGQTFYA (SEQ ID NO:3). Alternatively, the polypeptide induces an immune response specifically recognizing the HIV viral epitope targeted by human monoclonal antibody 2219. The immunogenic polypeptide can comprise the amino acid sequence of TPQNITDLCA EYHNTQIHTL NDKIFSYTES LAGKREMAII TFCTRPSNNT RKSINFGPGQ TFYATGEIIG DIRQAHCATF QVEVPGSQHI DSQKKAIERM KDTLRIAYLT EAKVEKLCVW NNKTPRAIAA ISMAN (SEQ ID NO:4).

In one embodiment, the immunogenic polypeptide according to the present invention is in cyclized form. Cyclic peptides according to the present invention are composed of or include sequences designed by the invented method. These peptides may be synthesized and include two Cys residues that bond via a disulfide linkage forming the cyclic peptide. Alternatively, the peptide may be cyclized by chemical means without relying upon disulfide bonding of two Cys residues, for example, by introduction of a linker.

The present invention relates to an immunogen that induces broadly neutralizing antibodies against HIV-1. In one embodiment, the scaffold protein comprises all or most of the scaffold polypeptide Cholera Toxin subunit B (CTB) (GenBank Accession No. AAC34728, which is hereby incorporated by reference in its entirety), having the following amino acid sequence:

```
                                     (SEQ ID NO: 5)
MIKLKFGVFF TVLLSSAYAH GTPQNITDLC AEYHNTQIHT

LNDKIFSYTE SLAGKREMAI

ITFKNGATFQ VEVPGSQHID SQKKAIERMK DTLRIAYLTE

AKVEKLCVWN NKTPHAIAAI SMAN 124
```

According to certain embodiments of the present invention, the scaffold protein is cholera toxin subunit B (CTB) or a homologue thereof which shares at least 50%, 60%, 70%, 80%, 90%, or 95% amino acid sequence identity with CTB, or a fragment or conservative amino acid substitution variant thereof, which homologue fragment or variant retains the immunogenicity and GM1-binding properties of CTB. In one particular embodiment, the scaffold protein is cholera toxin subunit B (CTB).

Other useful scaffolds for the construct of the present invention include a family of closely related bacterial proteins which are homopentamers of relatively small subunits (~100 aa). It is preferred that the scaffold protein be one that, like CTB, is highly immunogenic and capable of enhancing the immunogenicity of any heterologous sequences fused to or inserted in it (whether internally or at either terminus).

A preferred scaffold protein is one that is immunogenic. One preferred embodiment is a scaffold protein that, like CTB, includes a binding site for the oligosaccharide portion of ganglioside GMi in membranes. X-ray analysis of CTB revealed an oligosaccharide binding site formed by residues E51, Q56, H57, Q61, W88, N90, K91 (Sixma et al., "Lactose Binding to Heat Labile Enterotoxin Revealed by X-Ray Crystallography," Nature 355:561-64 (1992), which is hereby incorporated by reference in its entirety).

Despite the use of CT as an immunogenic scaffold (see Background section), it was nevertheless unexpected to find that various HIV-I V3 loop peptides and molecules derived therefrom, such as cyclic peptides and reverse peptides (discussed below), showed potent binding by anti HIV-I mAbs, and induced more broadly-neutralizing Ab responses against V3's of various viral subtypes or clades.

Other polypeptides that share the advantageous properties of CTB are also intended within the scope of the present invention as scaffolds for various V3 molecules to produce broadly neutralizing Ab response in vivo. One example of an *E. coli* enterotoxin useful as a scaffold protein herein is heat-labile enterotoxin B subunit, also referred to as LTc B (GenBank Accession No. AAC60441, which is hereby incorporated by reference in its entirety). A 124 residue polypeptide (SEQ ID NO:6) of this sequence is shown below.

```
MNKVKCYVLF TALLSSLCAY GAPQSITELC SEYRNTQIYT

INDKILSYTE SMAGKREMVI ITFKSGATFQ VEVPGSQHID

SQKKAIERMK DTLRITYLTE TKIDKLCVWN NKTPNSIAAI SMEN
```

According to certain embodiments of the present invention, the scaffold protein is *E. coli* enterotoxin or a homologue thereof which shares at least 50%, 60%, 70%, 80%, 90%, or 95% amino acid sequence identity with *E. coli* enterotoxin, or a fragment or conservative amino acid substitution variant thereof.

The following terms are used in the disclosure of sequences and sequence relationships between two or more nucleic acids or polypeptides: (a) "reference sequence", (b) "comparison window", (c) "sequence identity", (d) "percentage of sequence identity", and (e) "substantial identity."

As used herein, "reference sequence" is a defined sequence used as a basis for sequence comparison. A reference sequence may be a subset of the entirety of a specified sequence; for example, as a segment of a full-length cDNA or other polynucleotide sequence, or the complete cDNA or polynucleotide sequence. The same is the case for polypeptides and their amino acid sequences.

As used herein, "comparison window" includes reference to a contiguous and specified segment of a polynucleotide or amino acid sequence, wherein the sequence may be compared to a reference sequence and wherein the portion of the sequence in the comparison window may comprise additions or deletions (i.e., gaps) compared to the reference sequence (which does not comprise additions or deletions) for optimal alignment of the two sequences. Generally, the comparison window is at least 20 contiguous nucleotides or amino acids in length, and optionally can be 30, 40, 50, 100, or longer. Those of skill in the art understand that to avoid a high similarity to a reference sequence due to inclusion of gaps in the sequence a gap penalty is typically introduced and is subtracted from the number of matches. Methods of alignment of nucleotide and amino acid sequences for comparison are well-known in the art. For comparison, optimal alignment of sequences may be done using any suitable algorithm, of which the following are examples:

(a) the local homology algorithm ("Best Fit") of Smith et al., "Comparison of Biosequences," *Adv. Appl. Math.* 2(4): 482-89 (1981), which is hereby incorporated by reference in its entirety;

b) the homology alignment algorithm (GAP) of Needleman et al., "Algorithm," *J. Mol. Biol.* 48:443-453 (1970), which is hereby incorporated by reference in its entirety; or (c) a search for similarity method (FASTA and TFASTA) of Pearson et al., "Improved Tools for Biological Sequence Comparison," *Proc. Nat'l Acad. Sci.* 85(8):2444-8 (1988), which is hereby incorporated by reference in its entirety. In a preferred method of alignment, Cys residues are aligned. Computerized implementations of these algorithms, include, but are not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG) (Madison, Wis.). The CLUSTAL program is described by Higgins et al., "CLUSTAL: A Package for Performing Multiple Sequence Alignment on a Microcomputer," *Gene* 73:237-244 (1988); Higgins et al., "Fast and sensitive multiple sequence alignments on a microcomputer," *CABIOS* 5:151-153 (1989); Corpet et al., *Nucl Acids Res* 76:881-90 (1988); Huang et al., *CABIOS* 8:155-65 (1992); and Pearson et al., "Using the FASTA Program to Search Protein and DNA Sequence Databases," *Methods in Mol. Bio.* 24:307-331 (1994), which are hereby incorporated by reference in their entirety). A preferred program for optimal global alignment of multiple sequences is PileUp (Feng & Doolittle, "Progressive Sequence Alignment as a Prerequisite to Correct Phylogenetic Trees," *J Mol. Evol.* 25:351-360 (1987), which is hereby incorporated by reference in its entirety), which is similar to the method described by Higgins et al., "Fast and Sensitive Multiple Sequence Alignments on a Microcomputer," *CABIOS* 5:151-153 (1989), which is hereby incorporated by reference in its entirety).

The BLAST family of programs which can be used for database similarity searches includes: BLASTN for nucleotide query sequences against database nucleotide sequences; BLASTX for nucleotide query sequences against database protein sequences; BLASTP for protein query sequences against database protein sequences; TBLASTN for protein query sequences against database nucleotide sequences; and TBLASTX for nucleotide query sequences against database nucleotide sequences. See, for example, Ausubel et al., eds., *Current Protocols in Molecular Biology*, Chapter 19, Greene Publishing and Wiley-Interscience, New York (1995) or most recent edition, which is hereby incorporated by reference in its entirety. Unless otherwise stated, sequence identity/similarity values provided herein, typically in percentages, are derived using the BLAST 2.0 suite of programs (or updates thereof) using default parameters. Altschul et al., "Gapped BLAST and PSI-BLAST: A New Generation of Protein Database Search Programs," *Nucl Acids Res.* 25:3389-3402 (1997), which is hereby incorporated by reference in its entirety.

As is known in the art, BLAST searches assume that proteins can be modeled as random sequences. However, many real proteins comprise regions of nonrandom sequence which may include homopolymeric tracts, short-period repeats, or regions rich in particular amino acids. Alignment of such regions of "low-complexity" regions between unrelated proteins may be performed even though other regions are entirely dissimilar. A number of low-complexity filter programs are known that reduce such low-complexity alignments. For example, the SEG (Wooten et al., *Comput. Chem.* 77:149-63 (1993), which is hereby incorporated by reference in its entirety) and XNU (Claverie et al, *Comput. Chem.* 77:191-201 (1993), which is hereby incorporated by reference in its entirety) low-complexity filters can be employed alone or in combination.

As used herein, "sequence identity" or "identity" in the context of two nucleic acid or amino acid sequences refers to the nucleotides or amino acid residues in the two sequences which are the same when the full sequence is aligned for maximum correspondence over a specified comparison window. It is recognized that when using percentages of sequence identity for proteins, a residue position which is not identical often differs by a conservative amino acid substitution, where a substituting residue has similar chemical properties (e.g., charge, hydrophobicity, etc.) and therefore, does not change the functional properties of the polypeptide. Where sequences differ in conservative substitutions, the % sequence identity may be adjusted upwards to correct for the conservative nature of the substitution, and be expressed as "sequence similarity" or "similarity" (combination of identity and differences that are conservative substitutions). Means for making this adjustment are well-known in the art. Typically, this involves scoring a conservative substitution as a partial rather than as a full mismatch, thereby increasing the percentage sequence identity. Thus, for example, where an identical amino acid is given a score of "1" and a non-conservative substitution is given a score of "0" zero, a conservative substitution is given a score between 0 and 1. The scoring of conservative substitutions is calculated, e.g., according to the algorithm of Meyers et al., "Optimal Alignments in Linear Space," *CABIOS* 4:11-17 (1988), which is hereby incorporated by reference in its entirety, as implemented in the program PC/GENE (Intelligenetics, Mountain View, Calif., USA).

As used herein, "percentage of sequence identity" refers to a value determined by comparing two optimally aligned sequences over a comparison window, wherein the portion of the nucleotide or amino acid sequence in the comparison window may comprise additions or deletions (i.e., gaps) as compared to the reference sequence (which lacks such additions or deletions) for optimal alignment, such as by the GAP algorithm (supra). The percentage is calculated by determining the number of positions at which the identical nucleotide or amino acid residue occurs in both sequences to yield the number of matched positions, dividing that number by the total number of positions in the window of comparison and multiplying the result by 100, thereby calculating the percentage of sequence identity. The term "substantial identity" of two sequences means that a polynucleotide or polypeptide comprises a sequence that has at least 60%, preferably at least 70%, more preferably at least 80%, even more preferably at least 90%, and most preferably at least 95% sequence identity to a reference sequence using one of the alignment programs described herein using standard parameters. Values can be appropriately adjusted to determine corresponding identity of the proteins encoded by two nucleotide sequences by taking into account codon degeneracy, amino acid similarity, reading frame positioning, etc.

One indication that two nucleotide sequences are substantially identical is if they hybridize to one other under stringent conditions. Because of the degeneracy of the genetic code, a number of different nucleotide codons may encode the same amino acid. Hence, two given DNA sequences could encode the same polypeptide but not hybridize under stringent conditions. Another indication that two nucleic acid sequences are substantially identical is that the polypeptide encoded by the first nucleic acid is immunologically cross reactive with the polypeptide encoded by the second nucleic acid. Clearly, then, two peptide or polypeptide sequences are substantially identical if one is immunologically reactive with antibodies raised against the other. A first peptide is substantially identical to a second peptide, if they differ only by a conservative substitution. Peptides which are "substantially similar" share sequences as noted above except that nonidentical residue positions may differ by conservative substitutions.

In a preferred embodiment, the length of a sequence being compared is at least 30%, preferably at least 40%, more preferably at least 50%, even more preferably at least 60%, and even more preferably at least 70%, 80%, or 90% of the length of the reference sequence, for example, wild-type CTB.

The comparison of sequences and determination of percent identity between two sequences can be accomplished using a mathematical algorithm. In a preferred embodiment, the percent identity between two amino acid sequences is determined using the Needleman et al. (*J Mol. Biol.* 45:444-453 (1970), which is hereby incorporated by reference in its entirety), algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the ALIGN program (version 2.0), using a PAM 120 weight residue table, a gap length penalty of 12 and a gap penalty of 4.

The scaffold polypeptide or protein of the present invention preferably has at least about 50% sequence identity with CTB (or with LTc B). More preferably, the sequence identity with CTB is 55%, 60%, 65%, 70%, 75%, 80%, 85%, 90%, 91%, 92%, 93%, 94%, 95%, 96%, 97%, 98%, or 99% (or any intermediate value between the percent identity shown above).

Direct insertion, as opposed to the more commonly used fusion via a linker, allows the immunogenic scaffold to impose constraints on the termini of the V3 loop. Appropriate choice of the insert length and position are exploited to induce in the loop the desired conformation in which conserved epitopes are exposed. Exposure of these conserved epitopes confers on the immunogen the ability to induce a broadly neutralizing Ab response.

Available structural information on V3 peptides complexed with neutralizing antibodies suggests two different binding modes and epitopes associated with broad neutralization:

(1) Complex with Ab447-52D (Stanfield, R L et al., "Structural Rationale for the Broad Neutralization of HIV-1 by Human Monoclonal Antibody 447-52D," *Structure* 72:193-204 (2004), which is hereby incorporated by reference in its entirety). The epitope consists primarily of the backbone atoms of V3 loop (2) Complex with Ab2219 (Stanfield, R L et al., "Crystal Structures of Human Immunodeficiency Virus Type 1 (HIV-1) Neutralizing Antibody 2219 in Complex with Three Different V3 Peptides Reveal a New Binding Mode for HIV-1 Cross-Reactivity," *J. Virol.* 80:6093-6105 (2006), which is hereby incorporated by reference in its entirety). Antibody contacts mostly side-chain atoms of V3, but the amino acids involved are highly conserved in the V3 sequence-four side-chains that form a hydrophobic cluster and two positively charged side-chains.

Molecular modeling is used to test in-silico, whether various insertion positions in the scaffold and different loop lengths result in loop conformations that present one of these two conserved epitopes. Specifically, the present inventors have employed two approaches: (A) The scaffold is scanned for amino-acid positions that can be superimposed on the termini of the loop as observed in the V3/antibody complex. When superposition within small tolerances (≤0.5 A root mean square deviation (RMSD) for the terminal residues is achieved, the model is evaluated for the absence of clashes with the scaffold structure. (B) The loop is inserted in a random conformation and subjected to conformational sampling. Low energy conformations generated during sampling are compared to the desired V3 conformation as observed in the V3/antibody complex. Sampling is over a restricted energy range. When the construct is such that conformations within 1.0A backbone RMSD of the desired V3 conformation are identified in the simulation, a model of the immunogen-antibody complex is built to ensure that the scaffold does not interfere with the V3 loop/antibody binding.

The foregoing descriptions of sequence similarity, homology, etc., with respect to the scaffold protein are also applicable to the HIV-I antigenic sequences, with an emphasis on V3 loop peptide sequences. Various approaches are described herein to generate novel V3 peptide sequences, which include variants and functional derivatives (e.g., cyclic peptides, reverse peptides, etc., that maintain the correct structural characteristic so that the peptide or derivative is antigenic, and, more preferably, immunogenic in a subject in whom a broadly-reactive anti-HIV-I antibody response is sought). A V3 peptide (which term is defined as including a variant or functional derivative of a natural V3 peptide is then used to create an producing recombinant immunogenic polypeptide by introduction into the sequence and tertiary structure of a scaffolding protein. The descriptions herein utilize particular sequences, such as consensus sequences of particular viral subtypes or clades, or sequences taken from particular HIV-I strains. It should be understood, however, that the present invention also comprehends homologues, fragments, mutants or variants (such as conservative amino acid substitution variants) as indicated above and as discussed further below in describing cyclic and reverse peptides.

The smaller the scaffold used for the construct, the fewer are the number of potential "irrelevant" epitopes it carries. In a preferred embodiment, the design of a construct uses a relatively small oligomeric scaffold, generally >50 residues and less than about 1000 residues, preferably at least about 100 residues into which is inserted the V3 peptide which term is defined as including a variant or functional derivative of a natural V3 peptide.

The V3 peptide is preferably inserted directly into the scaffold's tertiary structure. This yields a polypeptide in which an exceptionally high fraction of the molecular surface presents relevant epitopes, in this case V3 epitopes that (1) are recognized by broadly-reactive neutralizing anti-gp120 antibodies and (2) can elicit anti-HIV-1 antibody responses that preferably are broadly-reactive and neutralize the virus. A "broadly reactive" or "broadly neutralizing" antibody or antibody response is an antibody or response that results in binding and neutralization of at least one group of heterologous HIV-I viruses, that are members of a different subtype of Glade than that of the source of the immunizing antigen, generally a V3 epitope. Preferably a broadly reactive antibody neutralizes viruses of at least 2 subtypes or clades, or viruses of at least 3 or 4 subtypes or clades. Preferably the antibodies induced by the present immunogenic polypeptides are mucosal antibodies that are capable of neutralizing HIV-1 virions in mucosal sites or spaces. Mucosal immunity is well-known in the art, and is described in standard textbooks of immunology, for example, A. K. Abbas et al., CELLULAR AND MOLECULAR IMMUNOLOGY (Fourth ed., W.B. Saunders Co., Philadelphia 2000); CA. Janeway et al., IMMUNOBIOLOGY. THE IMMUNE SYSTEM IN HEALTH AND DISEASE (Fourth ed., Garland Publishing Co., New York 1999); I. Roitt et al., IMMUNOLOGY (current ed., CV. Mosby Co., St. Louis, Mo. 1999), which are hereby incorporated by reference in their entireties and also includes more recent editions of these texts.

Recent references that disclose DNA and protein immunization to induce anti-HIV-1 immunity, particularly neutralizing antibodies, include Vaine et al., "Improved Induction of Antibodies Against Key Neutralizing Epitopes by Human Immunodeficiency Virus Type 1 gp120 DNA Prime-Protein Boost Vaccination Compared to gp120 Protein-Only Vaccination," *J. Virol.* 82:7369-78 (2008); Wang et al., "Cross-Subtype Antibody and Cellular Immune Responses Induced by a Polyvalent DNA Prime-Protein Boost HIV-1 Vaccine in Healthy Human Volunteers," *Vaccine* 26(31): 3947-57 (2008); Zolla-Pazner et al., "Focusing the Immune Response on the V3 Loop, a Neutralizing Epitope of the HIV-1 gp120 Envelope," *Virology* 372(2):233-46 (2008); Lu, "Combination DNA Plus Protein HIV Vaccines," *Springer Semin. Immunopathol.* 28(3):255-65 (2006); Wang et al., "Polyvalent HIV-1 Env Vaccine Formulations Delivered by the DNA Priming Plus Protein Boosting Approach are Effective in Generating Neutralizing Antibodies Against Primary Human Immunodeficiency Virus Type 1 Isolates From Subtypes A, B, C, D and E," *Virology* 351(1):34-47 (2006); Wang et al., "Enhanced Immunogenicity of gp120 Protein When Combined with Recombinant DNA Priming to Generate Antibodies that Neutralize the JR-FL Primary Isolate of Human Immunodeficiency Virus Type 1," *J. Virol.* 79:7933-37 (2005), all of which are hereby incorporated by reference in their entireties.

As exemplified below with Immunogen I, the V3 surface constitutes 51% or 6%, respectively of the total solvent-accessible surface of the immunogen. This high proportion of V3 epitopes on the immunogen surface will result in highly focused antibody response when the immunogen is administered.

The peptide compositions of the present invention may be synthesized using organic synthesis and peptide synthesis, which are known to those of skill in the art. New methods for restricting the secondary structure of peptides and proteins are highly desirable for the rational design of therapeutically useful conformationally-restricted (or "locked") pharmacophores. Examples include an analogue of eel calcitonin, [Asu$^{1,7}$]-eel calcitonin, in which α-aminosuberic acid (Asu) replaces the Cys residues at positions 1 and 7 (Morikawa, et al., "Synthesis of Eel-Calcitonin and [Asu$^{1,7}$]-Eel Calcitonin: Contribution of the Disulfide Bond to the Hormonal Activity," *Experientia* 32:1104-6 (1976), which is hereby incorporated by reference in its entirety). This analogue had significant biological activity, leading the authors to conclude that the disulfide bond in calcitonin is not essential for biological activity as long as the specific conformation of the peptide is maintained by an intramolecular bridge.

The purely chemical approaches for restricting secondary structure often requires extensive multistep syntheses (Olson et al., "Design and Synthesis of a Protein β-turn Mimetic," *J. Am. Chem. Soc.* 112:323 (1990), which is hereby incorporated by reference in its entirety). An alternative approach involves installing covalent bridges in peptides. However, due to the sensitivity of the peptide backbone and side chains, this method necessitates careful protection/deprotection strategies. For example, this problem occurred in the preparation of polymethylene analogues of [Arg$^8$]vasopressin Asu replaced Cys residues at positions 1 and 7 and in which the N-terminal amino group was removed (Hase et al., "Synthesis of a Biologically Active Analog of Deamino-8-arginine-vasopressin Which Does not Contain a Disulphide Bond," *Experientia* 25:1239-40 (1969); Hase et al., "1,6-Aminosuberic Acid Analogs of Lysine- and Arginine-vasopressin and -Vasotocin. Synthesis and Biological Properties," *J. Amer. Chem. Soc.* 94:3590 (1972), which are hereby incorporated by reference in their entireties) yielding deamino-dicarba-Arg$^8$-vasopressin.

The peptide may include substitutions of residues from a "natural" natural loop sequence or chemical modification of side chains or introduction other organic groups to enhance stability and antigenic/immunogenic function as described herein.

Covalent linkages can, in selected instances, be established using other chemical methods, for example, by lactam formation between carboxylic acid and amine side chains $$X^1X^2X^3X^4X^5X^6X^7...X^n$$
$$\underbrace{\qquad\qquad}_{\text{Linker}}$$

wherein n is preferably between 10 and 23 (i.e., a 10-mer to a 23-mer peptide). The linker is optional, particularly if $X^1$ and $X^n$ are each Cys. In one embodiment, all of $X^1$ through $X^n$ represent amino acids (L- or D-) corresponding to all or part of the V3 loop of the HIV-1 virus of the desired strain, or subtype consensus sequence.

The general guiding principles determining the design of useful cyclic peptides are well-known in the art and are dictated by the need to maintain the Ab reactivity and immunogenicity of the loop peptide, particularly for induction of broadly reactive, neutralizing, and preferably mucosal antibodies while enhancing its stability as well as the ability to be inserted it into a desired scaffold protein without disrupting the "function" of the latter, i.e., immunogenicity and other binding characteristics of the scaffold such as the binding of recombinant V3-CTB to the glycolipid targets of CTB. In addition to testing a cyclic peptide serologically, it may be analyzed more extensively by structural (biophysical) techniques in solution or when bound to a characterizing broadly-reactive neutralizing mAb such as 3074, e.g., NMR spectroscopy or X-ray crystallographic methods.

Another aspect of the present invention relates to an immunogenic pharmaceutical composition comprising a recombinant immunogenic polypeptide according to the present invention and an immunologically and pharmaceutically acceptable vehicle or excipient. In one embodiment, the immunogenic polypeptide includes a designed loop peptide inserted into an immunogenic scaffold protein, where (a) the loop peptide has an amino acid sequence which presents the 3074 mAb- or the 2219/2557 mAb-targeted epitope of the HIV gp120 protein and not other epitopes of the HIV gp120 protein, and (b) when used as an immunogen, said polypeptide induces an antibody response which neutralizes heterologous HIV-1 viruses in a pattern similar to that observed for the 3074 mAb- or the 2219/2557 mAb-targeted epitope, respectively.

The compounds, compositions, or agents of the present invention can be administered locally or systemically. In particular, the compounds, compositions, or agents of the present invention can be administered intravenously, orally, transdermally, transmucosally, intrapleurally, intrathecally, by injection or infusion, by aerosol administration, intraperitoneally, orally, parenterally, for example, subcutaneously, intramuscularly, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions. The immunization protocol preferably includes at least one priming dose, followed by one or multiple boosting doses administered over time. An exemplary range for an immunogenically effective amount of the present immunogenic polypeptides is about 5 to about 500 μg/kg body weight. A preferred range is about 10-100 μg/kg.

The active compounds or agents of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

These active compounds or agents may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds or agents of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Preferably, one or more unit doses of the immunogen are given at one, two or three time points. The optimal number and timing of boosts can readily be determined using routine experimentation. The immunogen may be given only as a booster, to a subject who has been primed with another form of the antigen, for example, a DNA vaccine that encodes either the V3-scaffold complex or another type of V3-endocing construct (see, e.g., WO 2008/005929A2 (including immunization schedules with different constructs to generate broadly-reactive neutralizing anti-gp120 antibodies) and U.S. Patent Application Publication No. US 2008/0279879, which are hereby incorporated by reference in their entireties). In particular, see Example VI of U.S. Patent Application Publication No. US 2008/0279879, which is hereby incorporated by reference in its entirety, and the references cited therein are informative.

Two boosts are preferred. Preferably, these boosts are separated by 2 weeks, more preferably by 4 weeks, and in other embodiments, 5, 6, 8, 12 weeks, etc., as needed to achieve and maintain the desired titers and breadth of the resulting antibodies. It is common that the antibody response remains at relatively high levels for months after the last boost. Blood samples for evaluation of antibody quantity and quality is preferably obtained about 2 weeks after the final boost. Adjuvants known in the art may be used during priming, boosting or both.

The present immunogenic composition may be administered together with an adjuvant or other immunostimulatory peptide or polypeptide that is different from the immunogenic peptide invention.

The one or more adjuvants or immunostimulating agents are preferably added to the fusion protein immunogens used for boosting the immune response. An adjuvant is any substance that can be added to an immunogen or to a vaccine formulation to enhance the immune-stimulating properties of the immunogenic moiety, such as a protein or polypeptide. Liposomes are also considered to be adjuvants (see, e.g., Gregoriades et al., *Immunological Adjuvants and Vaccines*, Plenum Press, New York (1989); Michalek et al., "Liposomes as Oral Adjuvants," *Curr. Top. Microbiol.*

*Immunol.* 146:51-58 (1989), which are hereby incorporated by reference in their entireties). Examples of adjuvants or agents that may add to the effectiveness of V3 DNA or peptides as immunogens include aluminum hydroxide, aluminum phosphate, aluminum potassium sulfate (alum), beryllium sulfate, silica, kaolin, carbon, water-in-oil emulsions, and oil-in-water emulsions. Other adjuvants are muramyl dipeptide (MDP) and various MDP derivatives and formulations, e.g., N-acetyl-D-glucosaminyl-(β1-4)-N-acetylmuramyl-L-alanyl-D-isoglutamine (GMDP) (Hornung et al., "Induction of a CD8+ Cytotoxic T Lymphocyte Response to Soluble Antigen Given Together With a Novel Muramyl Dipeptide Adjuvant, N-acetyl-D-glucosaminyl-(beta 1-4)-N-acetylmuramyl-L-alanyl-D-isoglutamine (GMDP)," *Ther. Immunol.* 2:7-14 (1995), which is hereby incorporated by reference in its entirety) or ISAF-1 (5% squalene, 2.5% pluronic L121, 0.2% Tween 80 in phosphate-buffered solution with 0.4 mg of threonyl-muramyl dipeptide; see Kwak et al., "Induction of Immune Response in Patients with B-Cell Lymphoma Against the Surface Immunoglobulin Idiotype Expressed by Their Tumors," *N. Engl. J. Med.* 327: 1209-1238 (1992), which is hereby incorporated by reference in its entirety) and monophosphoryl lipid A adjuvant solubilized in 0.02% triethanolamine. Other useful adjuvants are, or are based on, bacterial endotoxin, lipid X, whole organisms or subcellular fractions of the bacteria *Propionobacterium acnes* or *Bordetella pertussis*, polyribonucleotides, sodium alginate, lanolin, lysolecithin, vitamin A, saponin and saponin derivatives such as QS21 (White et al., "A Purified Saponin Acts as an Adjuvant for a T-Independent Antigen," *Adv. Exp. Med. Biol.* 303:207-210 (1991), which is hereby incorporated by reference in its entirety) which is now in use in the clinic (Helling et al., "GM2-KLH Conjugate Vaccine: Increased Immunogenicity in Melanoma Patients After Administration With Immunological Adjuvant QS-21," *Cancer Res.* 55:2783-2788 (1995); Davis et al., "Retreatments with Rituxan (rituximab, IDEC-C2B8) Have Significant Efficacy, Do Not Cause HAMA, and Are a Viable Minimally Toxic Alternative in Relapsed or Refractory Non-Hodgkin's Lymphoma (NHL)," *Blood* 90: 509A (1997), which are hereby incorporated by reference in their entireties), levamisole, DEAE-dextran, blocked copolymers or other synthetic adjuvants. Examples of commercially available adjuvants include (a) Amphigen®, an oil-in-water adjuvant made of de-oiled lecithin dissolved in an oil (see, e.g., U.S. Pat. No. 5,084,269 and U.S. Patent Application Publication No. 2005/0058667A1, which are hereby incorporated by reference in their entireties) and (b) Alhydrogel® which is an aluminum hydroxide gel. Aluminum is approved for human use. Adjuvants are available commercially from various sources, for example, Merck Adjuvant 65® (Merck and Company, Inc., Rahway, N.J.). The immunogenic material may be adsorbed to or conjugated to beads such as latex or gold beads, ISCOMs, and the like.

Suitable adjuvants include: (a) ISAF-1 (5% squalene, 2.5% pluronic L121, 0.2% Tween 80) in phosphate-buffered solution with 0.4 mg of threonyl-muramyl dipeptide; (b) de-oiled lecithin dissolved in an oil (e.g., AMPHIGENT™); (c) aluminum hydroxide gel; (d) a mixture of (b) and (c); (e) QS-21; (f) monophosphoryl lipid A adjuvant; and (g) incomplete Freund's adjuvant.

The immunogenic composition may also be supplemented with an immunostimulatory cytokine, lymphokine or chemokine. Preferred cytokines are GM-CSF (granulocyte-macrophage colony stimulating factor), interleukin 1, interleukin 2, interleukin 12, interleukin 18, or interferon-γ.

General methods to prepare immunogenic pharmaceutical compositions and vaccines are described in Remington's Pharmaceutical Science; Mack Publishing Company Easton, Pa. (latest edition), which is hereby incorporated by reference in its entirety.

Another aspect of the present invention relates to a method for inducing a broadly neutralizing antibody response against a designed loop in a subject. This method includes selecting a subject and administering to the selected subject an effective amount of the immunogenic polypeptide or the immunogenic pharmaceutical composition, of the present invention.

According to this aspect of the present invention, the selected subject may be infected with HIV, infected with a form of HIV-1 heterologous to that from which the immunogenic polypeptide is derived, or at risk for infection with HIV.

From the foregoing, it should be appreciated that the present invention also relates to a method of imparting resistance against HIV to a mammal. This method is carried out by administering to a mammal a vaccine including the immunogenic polypeptide of the present invention under conditions effective to induce a protective immune response against HIV.

A further aspect of the present invention relates an isolated antibody raised against an immunogenic polypeptide of the present invention, or antibody fragment thereof, which antibody or antibody fragment is capable of specifically binding and neutralizing HIV.

The antibodies of the present invention can be polyclonal antibodies or monoclonal antibodies.

Various methods of producing antibodies with a known antigen are well-known to those ordinarily skilled in the art (ANTIBODIES: A LABORATORY MANUAL (Harlow & Lane eds., 1988), which is hereby incorporated by reference in its entirety). In particular, suitable antibodies may be produced by chemical synthesis, by intracellular immunization (i.e., intrabody technology), or preferably, by recombinant expression techniques. Methods of producing antibodies may further include the hybridoma technology well-known in the art.

In particular, monoclonal antibody production may be effected by techniques which are well-known in the art. Basically, the process involves first obtaining immune cells (lymphocytes) from the spleen of a mammal (e.g., mouse) which has been previously immunized with the chimeric protein either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler & Milstein, "Continuous Cultures of Fused Cells Secreting Antibody of Predefined Specificity," *Nature*, 256: 495-497 (1975), which is hereby incorporated by reference in its entirety.

Mammalian lymphocytes are immunized by in vivo immunization of the animal (e.g., a mouse) with the chimeric protein or DNA vaccine of the present invention. Following a sufficient number of immunizations (i.e., one or more), the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents (see Milstein & Kohler, "Derivation of Antibody-producing Tissue Culture and Tumor Lines by Cell Fusion," *Eur. J. Immunol.* 6:511-519 (1976), which is hereby incorporated by reference in its entirety). This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known. Typically, such antibodies can be raised by administering the chimeric protein or DNA vaccine of the present invention subcutaneously to New Zealand white rabbits which have first been bled to obtain pre-immune serum. The antigens can be administered at a total volume of 100 µl per site at multiple sites. Each injected material may contain synthetic surfactant adjuvant pluronic polyols, or pulverized acrylamide gel containing the purified chimeric protein or DNA vaccine. The rabbits are then bled two weeks after the first injection and periodically boosted with the same antigen three times every six weeks. Boosting may not be required with the DNA vaccine. A sample of serum is then collected 10 days after each boost. Polyclonal antibodies are then recovered from the serum by affinity chromatography using the corresponding chimeric protein to capture the antibody. Ultimately, the rabbits are euthanized with pentobarbital 150 mg/Kg IV. This and other procedures for raising polyclonal antibodies are disclosed in ANTIBODIES: A LABORATORY MANUAL (Harlow & Lane eds., 1988), which is hereby incorporated by reference in its entirety.

In addition to utilizing whole antibodies, the present invention also encompasses use of binding portions of such antibodies. Such binding portions include Fab fragments, F(ab)$_2$ fragments, Fab' fragments, F(ab')$_2$ fragments, Fd fragments, Fd' fragments, Fv fragments, and minibodies, e.g., 61-residue subdomains of the antibody heavy-chain variable domain (Pessi et al., "A Designed Metal-binding Protein with a Novel Fold," *Nature* 362:367-369 (1993), which is hereby incorporated by reference in its entirety). Domain antibodies (dAbs) are also suitable for the methods of the present invention (Holt et al., "Domain Antibodies: Proteins for Therapy," *Trends Biotechnol.* 21:484-90 (2003), which is hereby incorporated by reference in its entirety). These antibody fragments can be made by conventional procedures, such as proteolytic fragmentation procedures, as described in J. Goding, MONOCLONAL ANTIBODIES: PRINCIPLES AND PRACTICE 98-118 (1984), which is hereby incorporated by reference in its entirety.

The antibodies may be from humans, or from animals other than humans, preferably mammals, such as rat, mouse, guinea pig, rabbit, goat, sheep, and pig, or avian species such as chicken. Preferred are mouse monoclonal antibodies and antigen-binding fragments or portions thereof. In addition, chimeric antibodies and hybrid antibodies are embraced by the present invention. Techniques for the production of chimeric antibodies are described in, e.g., Morrison et al., "Chimeric Human Antibody Molecules: Mouse Antigen-binding Domains with Human Constant Region Domains," *Proc. Nat'l Acad. Sci. USA* 81:6851-5 (1984), Neuberger et al., "Recombinant Antibodies Possessing Novel Effector Functions," *Nature* 312:604-8 (1984), and Takeda et al., "Construction of Chimaeric Processed Immunoglobulin Genes Containing Mouse Variable and Human Constant Region Sequences," *Nature* 314:452-4 (1985), each of which is hereby incorporated by reference in its entirety. For human therapeutic purposes, humanized antibodies or fragments are preferred.

Further, single chain antibodies are also suitable for the present invention (e.g., U.S. Pat. No. 5,476,786 to Huston and U.S. Pat. No. 5,132,405 to Huston & Oppermann; Huston et al., "Protein Engineering of Antibody Binding Sites: Recovery of Specific Activity in an Anti-digoxin Single-chain Fv Analogue Produced in *Escherichia coli*," *Proc. Nat'l Acad. Sci. USA* 85:5879-83 (1988); U.S. Pat. No. 4,946,778 to Ladner et al.; Bird et al., "Single-chain Antigen-binding Proteins," *Science* 242:423-6 (1988); Ward et al., "Binding Activities of a Repertoire of Single Immunoglobulin Variable Domains Secreted from *Escherichia coli*," *Nature* 341:544-6 (1989), each of which is hereby incorporated by reference in its entirety). Single chain antibodies are formed by linking the heavy and light immunoglobulin chain fragments of the Fv region via an amino acid bridge, resulting in a single chain polypeptide. Univalent antibodies are also embraced by the present invention.

A pharmaceutical composition comprising the antibodies or antibody fragments of the present invention can be administered to an individual to provide passive immunity against HIV infection. The antibodies or antibody fragments can be administered to a patient exposed to HIV to afford passive immunity against HIV. Thus, a further aspect of the present invention relates to treatment of a HIV infection by administering to a patient the antibodies or antibody fragments (or composition containing the same) under conditions effective to reduce or neutralize the HIV infection as compared to a patient where such treatment is not administered. Administration can be carried out by any suitable means, but preferably parenterally, subcutaneously, intravenously, intramuscularly, intraperitoneally, by intracavitary or intravesical instillation, intraarterially, intralesionally, by application to mucous membranes, or directly to a site of infection.

Yet another aspect of the present invention relates to a kit. The kit includes separate compartments in close proximity. The separate compartments include one or more unit dosages of the immunogenic polypeptide according to the present invention or the immunogenic pharmaceutical composition, according to the present invention. The kit also includes instructions for administering the immunogenic polypeptide or immunogenic pharmaceutical composition to a subject for inducing a broadly-neutralizing antibody response.

Yet a further aspect of the present invention relates to a method of preparing an immunogenic polypeptide capable of generating an immune response against an antigen of interest. This method includes identifying the known epitopes of the antigen of interest, providing candidate agents in which all but one of the identified known epitopes of the antigen of interest are eliminated, and immunizing a mammal with the candidate agents. Serum from the immunized mammal is recovered, and it is determined if the recovered serum recognizes the antigen of interest. Candidate agents whose serum is recognized by the antigen of interest are identified as immunogenic polypeptides.

The antigen of interest may include any human pathogen. The antigen of interest can be derived from a virus. Exemplary viruses include, without limitations, Calicivirus, Chikungunya virus, Cytomegalovirus, Dengue virus, Eastern Equine Encephalitis virus, Ebola virus, Epstein-Barr virus, Hantaan virus, Hepatitis A virus, Hepatitis B virus, Hepatitis C virus, Hepatitis D virus, Hepatitis E virus, Herpes simplex virus, Human Immunodeficiency virus (HIV-1), Human Papillomavirus, Influenza virus, Japanese encephalitis virus, Junin virus, Lassa virus, Marburg virus, Measles virus, Metapneumovirus, Nipah virus, Newcastle disease virus, Norwalk virus, Parainfluenza virus, Poliovirus, Rabies virus, Respiratory Syncytial virus, Rift Valley Fever virus, Rotavirus, Rubella virus, Sendai virus, Severe Accute Respiratory Syndrome (SARS Co-V), Tick-borne Encephalitis virus, Varicella zoster virus, Venezuelan Equine Encephalitis virus, Yellow Fever virus, Western Equine Encephalitis virus, and West Nile virus.

Alternatively, the antigen of interest can be derived from a bacteria. Exemplary bacteria include, without limitation, *Bacillus anthracis*, *Bordetella pertussis* B, *Borrelia burgdorferi*, *Chlamydia trachomatis*, *Clostridium difficile*, *Clostridium tetani*, *Candida albicans*, *Corynebacterium diphtheriae*, *Cryptococcus neoformans*, *Entamoeba histolytica*, *Escherichia coli*, *Francisella tularensis*, *Haemophilus influenzae* (nontypeable), *Helicobacter pylori*, *Histoplasma capsulatum*, *Moraxella catarrhalis*, *Mycobacterium leprae*, *Mycobacterium tuberculosis*, *Neisseria gonorrheae*, *Neisseria meningitides*, *Pseudomonas aeruginosa*, *Staphylococcus aureus*, Methicillin-resistant *Staphylococcus aureus*, *Streptococcus agalactiae*, *Streptococcus pneumoniae*, *Streptococcus pyogenes*, and *Yersinia pestis*.

In yet a further embodiment, the antigen of interest is an agricultural pathogen, such as farm animal pathogens.

In carrying out this method of the present invention, the determination of whether the recovered serum recognizes the antigen of interest is carried out by conducting an immunological binding reaction.

Advances in the field of immunology have allowed more thorough and sensitive evaluations of cellular immune responses to candidate HIV vaccines when designing and selecting immunogens. Such assays, as intracellular staining (e.g., flow cytometry) and ELISPOT (an enzyme-linked immunosorbent assay format), allow detecting and counting cells producing cytokines in response to antigens. For example, isolation of splenocytes or peripheral blood monocyte cells (PBMCs) from an animal or human followed by in vitro challenge with an appropriately presented HIV epitope such as those in the V3 loop, and finally testing by ELISPOT and/or intracellular cytokine staining (ICS), can determine the potential for a cell-mediated immune response in vaccine recipients.

Preferably, ELISA and Western blots are used to assess the antibody response. These method can assess antibody binding, antibody neutralizing capability, antibody-mediated fusion inhibition, and antibody-dependent cytotoxicity. These methods are conventional in the art and are, therefore, not described in any significant detail here.

An MT-2 assay can be performed to measure neutralizing antibody responses. Antibody-mediated neutralization of a selected strains or isolates of HIV-1 can be measured in an MT-2 cell-killing assay (Montefiori et al., "Evaluation of Antiviral Drugs and Neutralizing Antibodies to Human Immunodeficiency Virus by a Rapid and Sensitive Microtiter Infection Assay," *J. Clin. Microbiol.* 26:231-7 (1988), which is hereby incorporated by reference in its entirety. HIV-1$_{IIIB}$ and HIV-1$_{MN}$ induce the formation of syncytia in MT-2 T cells. The inhibition of the formation of syncytia by the sera shows the activity of neutralizing antibodies present within the sera, induced by vaccination. Immunized test and control sera can be exposed to virus-infected cells (e.g., cells of the MT-2 cell line). Neutralization can be measured by any method that determines viable cells, such as staining, e.g., with Finter's neutral red. Percentage protection can be determined by calculating the difference in absorption ($A_{540}$) between test wells (cells+virus) and dividing this result by the difference in absorption between cell control wells (cells only) and virus control wells (virus only). Neutralizing titers may be expressed, for example, as the reciprocal of the plasma dilution required to protect at least 50% of cells from virus-induced killing.

Combination of these features make the present immunogen uniquely capable of inducing a strong, broadly neutralizing antibody response against gp120 and thereby generate a more effective state of immunity against HIV. Immunogen I, exemplified below, comprises a loop sequence: CTRPSNNTTESINIGPGQTFYATGEI-IGDIRQAHC (SEQ ID NO:7) inserted into a scaffold.

The present invention relates also to the method of designing the loop sequence such that it will elicit specific antibody responses of interest in animal serum after inoculation, such as a 3074-like antibody response. In one embodiment, the method is composed of:

a) a loop with initially the same amino acid sequence as the V3 loop of the consensus subtype C HIV gp120 sequence;

b) identifying all of the known neutralization epitopes in the sequence of the loop by searching it with a library of neutralization epitope sequence motifs;

c) choosing point mutations in the sequence that destroy or reduce all but the desired epitope sequence motif; and d) making additional point mutations that do not affect the epitopes but reduce the ancillary charged (electropositive or electro-negative) residues in the loop to polar or uncharged residues.

The known sequence motifs for Ab epitopes in the V3 loop of gp120 used to design the invented 3074 exclusive immunogen are:

| Monoclonal antibody | Specific sequence motif |
| --- | --- |
| 268-D | [K, R]10, [H, R]13, P16, R18 |
| 447-52D | P16, R18 |
| 537-10D | R9, [I, M]14, P16, R18 |
| 2219 | R9, K10, [I, V]12, [Y, F]21 |
| 2557 | K10, [I, V]12, Y21 |
| 3074 | [I, L, M]14, P16, [F, W]20 |
| 3791 | S11, R13, I14, Q18 |

According to various aspects of the present invention, the desired epitope sequence motifs are targeted by the monoclonal antibodies selected from the group consisting of 268-D, 447-52D, 537-10D, 2219, 2557, 3074, 3791 (preferably 3074, 2219, or 2557), and combinations thereof. These and other monoclonal antibodies will be known to those of skill in the art and this list is not intended to be limiting.

Having now generally described the invention, the same will be more readily understood through reference to the following examples which are provided by way of illustration, and are not intended to be limiting of the present invention, unless specified.

EXAMPLES

Example 1

Preparation of the Recombinant CTB-Scaffold/3074-Epitope-Exclusive Loop Construct Immunogen I In this construct, the entire 35AA loop is inserted into the CTB polypeptide. It is missing the N-terminal 21 residues of native CTB. The loop peptide insert CTRPSNNTRKSIHIG-PGRAFYTTGEIIGDIRQAHC (SEQ ID NO:8) is shown in bold. The mutated residues to reduce or destroy the motif for the 2219 targeted epitope is underlined, the mutated residue to reduce or destroy the 447 targeted epitope is unbolded.

```
                                            (SEQ ID NO: 2)
TPQNITDLCA EYHNTQIHTL NDKIFSYTES LAGKREMAII

TFCTRPSNNT TESINIGPGQ TFYATGEIIG DIRQAHCATF

QVEVPGSQHI DSQKKAIERM KDTLRIAYLT EAKVEKLCVW

NNKTPRAIAA ISMAN
```

Example 2

Binding of Immunogen Construct to Human Anti-V3 Monoclonal Antibodies

Antigenic sequences were designed to mimic the structure of the V3 loop with mutations incorporated to eliminate shapes on the molecular surface corresponding to other known antibody neutralization epitopes and preserve shapes on the molecular surface corresponding to the neutralization epitopes targeted by the 3074 or 2219 antibodies respectively (FIG. 1). These designed antigens were inserted into an optimal location on the 3D structure of the cholera toxin B (CTB) protein, as previously described Totrov et al., "Structure-Guided Design and Immunological Characterization of Immunogens Presenting the HIV-1 gp120 V3 Loop on a CTB Scaffold," Virology 405(2):513-23 (2010), which is hereby incorporated by references in its entirety, to create a novel chimeric HIV-1 immunogen. The designed immunogen protein was expressed and purified and selectively bound 3074-like or 2219-like antibodies among a large panel of antibodies, indicating a successful design and successful folding of the protein (FIG. 2A). Furthermore, a chimeric HIV-1 derived pseudovirus bearing an exposed V3 crown loop whose sequence was identical to that of the designed antigenic loop in the protein immunogen was neutralized strongly only by the 3074 antibody and not by other mAbs, and a chimeric HIV-1 derived pseudovirus presenting the 2219 epitope design in its V3 loop similarly showed 2219 specific behavior (FIG. 2B).

Example 3

Immunization of Subjects with HIV-1 Subtype B V3-CTB Protein Complexes Induces Broadly Reactive Neutralizing Antibodies For a detailed description of methods of DNA and protein immunization against HIV-1 for generating neutralizing antibody responses, see publications, for example, Vaine et al., "Improved Induction of Antibodies Against Key Neutralizing Epitopes by Human Immunodeficiency Virus Type 1 gp120 DNA Prime-Protein Boost Vaccination Compared to gp120 Protein-Only Vaccination," J. Virol. 82:7369-78 (2008); Wang et al., "Cross-Subtype Antibody and Cellular Immune Responses Induced by a Polyvalent DNA Prime-Protein Boost HIV-1 Vaccine in Healthy Human Volunteers," Vaccine 26(31):3947-57 (2008); Zolla-Pazner et al., "Focusing the Immune Response on the V3 Loop, a Neutralizing Epitope of the HIV-1 gp120 Envelope," Virology 372(2):233-46 (2008); Lu, "Combination DNA Plus Protein HIV Vaccines," Springer Semin. Immunopathol. 28(3):255-65 (2006); Wang et al., "Polyvalent HIV-1 Env Vaccine Formulations Delivered by the DNA Priming Plus Protein Boosting Approach are Effective in Generating Neutralizing Antibodies Against Primary Human Immunodeficiency Virus Type 1 Isolates From Subtypes A, B, C, D and E," Virology 351(1):34-47 (2006); Wang et al., "Enhanced Immunogenicity of gp120 Protein When Combined with Recombinant DNA Priming to Generate Antibodies that Neutralize the JR-FL Primary Isolate of Human Immunodeficiency Virus Type 1," J. Virol. 79:7933-37 (2005), all of which are hereby incorporated by reference in their entireties.

Female New Zealand rabbits (2 kg) received three immunizations with DNA expression vectors expressing gp120 protein of the JR-FL strain of HIV-1 and codon-optimized for expression in rabbit cells. DNA was adsorbed to gold particles and administered intradermally via gene gun at times 0, 2 weeks, and 4 weeks. Each shot delivered 1 µg of DNA and a total of 36 non-overlapping shots were delivered to each rabbit at each of the three time points at the surface of shaved abdominal skin after animals are anesthetized according to IACUC approved protocols. Thus, the total dose per prime was 36 µg DNA.

Each animal received 100 µg of DNA distributed in non-overlapping sites on the surface of shaved abdominal skin after anesthesia according to IACUC approved protocols. Pre-immunization serum samples were collected immediately before the first priming immunization.

Six weeks after the last priming dose, rabbits were given booster immunizations with 36 µg of the indicated proteins (various V3-CTB complexes) followed by another boost 4 weeks later. Two weeks after the last boost, serum samples were obtained by venipuncture.

For a further description of this method of immunization, see, for example, Vaine et al., "Improved Induction of Antibodies Against Key Neutralizing Epitopes by Human Immunodeficiency Virus Type 1 gp120 DNA Prime-Protein Boost Vaccination Compared to gp120 Protein-Only Vaccination," J. Virol. 82:7369-78 (2008); Wang et al., "Cross-Subtype Antibody and Cellular Immune Responses Induced by a Polyvalent DNA Prime-Protein Boost HIV-1 Vaccine in Healthy Human Volunteers," Vaccine 26(31):3947-57 (2008); Zolla-Pazner et al., "Focusing the Immune Response on the V3 Loop, a Neutralizing Epitope of the HIV-1 gp120 Envelope," Virology 372(2):233-46 (2008); Lu, "Combination DNA Plus Protein HIV Vaccines," Springer Semin. Immunopathol. 28(3):255-65 (2006); Wang et al., "Polyvalent HIV-1 Env Vaccine Formulations Delivered by the DNA Priming Plus Protein Boosting Approach are Effective in Generating Neutralizing Antibodies Against Primary Human Immunodeficiency Virus Type 1 Isolates From Subtypes A, B, C, D and E," Virology 351(1):34-47 (2006); Wang et al., "Enhanced Immunogenicity of gp120 Protein When Combined with Recombinant DNA Priming to Generate Antibodies that Neutralize the JR-FL Primary Isolate of Human Immunodeficiency Virus Type 1," *J. Virol.* 79:7933-37 (2005), all of which are hereby incorporated by reference in their entireties.

Sera were tested in neutralization assays against pseudoviruses with V3 consensus sequence from various subtypes to test strength and breadth of the response, showing geometric mean titers. Stronger responses are reflected in 90% neutralization titers (vs. 50%), which are the dilutions resulting in 90% (or 50% neutralization). Results appear FIG. 3.

The same sera were tested in neutralization assays against primary HIV-1 isolates, a more rigorous test of the neutralizing capacity of the antibodies. The latter was expressed as the serum dilution resulting in an $IC_{50}$ (inhibitory concentration resulting in 50% neutralization, as above). Again, geometric mean titers were shown in FIG. 4. This approach accounts only for responding rabbits, whose titers were averaged.

In brief, it was observed that a broad and potent animal serum response was induced, both in neutralizing pseudoviruses and primary isolates, that the data shows contains largely 3074-like specificity in the serum antibodies, by design.

In an additional experiment, rabbits were immunized with the designed immunogens using a previously described immunofocusing protocol consisting of a DNA gp120 prime followed by a protein boost with each designed chimeric V3-CTB immunogen (Totrov et al., "Structure-Guided Design and Immunological Characterization of Immunogens Presenting the HIV-1 gp120 V3 Loop on a CTB Scaffold," *Virology* 405(2):513-23 (2010), which is hereby incorporated by reference in its entirety). The resulting rabbit serum potently neutralized 7 chimeric pseudoviruses each bearing the consensus sequence of a different HIV subtype in its V3 loop (FIG. 1). Notably, the pattern of neutralization of chimeric psVs differed significantly between the two different designs, with the 2219 epitope mimic (V3-CTB$^{2219}$) most potently neutralizing the subtype B consensus V3 loop and the 3074 epitope mimic (V3-CTB$^{3074}$) most potently neutralizing the subtype A chimeric psV. Both sera neutralized multiple strains of a limited panel of primary isolates and multiple strains in a standard panel of pseudoviruses (FIG. 2).

Tier 2 HIV-1 pseudoviruses are difficult to neutralize by most antibodies or sera, and Glade C viruses are the predominant circulating HIV-1 viruses in the pandemic. The equivalence of the specificity of the reactivity of an mAb in vitro against viruses and the specificity of mAbs elicited in serum against those same viruses can be assessed by comparing the pattern of neutralization across a panel of these difficult to neutralize and frequently masked viruses. The same three Clade C Tier 2 pseudoviruses that are neutralized by the pure 3074 antibody (Hioe et al., "Anti-V3 Monoclonal Antibodies Display Broad Neutralizing Activities against Multiple HIV-1 Subtypes," *PLoS ONE* 5(4): e10254 (2010), which is hereby incorporated by reference in its entirety) are also the only three Clade C Tier 2 pseudoviruses neutralized by the most potent individual rabbit serum induced by V3-CTB$^{3074}$ (FIG. 5). Both mAb and serum studies were performed by the independent central laboratory of the Vaccine Immune Monitoring Consortium of the Collaboration for AIDS Vaccine Discovery.

Finally, chimeric pseudoviruses (psV) were designed to eliminate or reduce one or both of the epitopes targeted by the mAbs 3074 and 2219. The neutralization by the animal serum resulting from immunization with V3-CTB$^{3074}$ was dramatically reduced in psV lacking only the 3074 epitope and completely eliminated against psV containing lacking both the 3074 and 2219 epitopes, while neutralization by the animal serum resulting from immunization with V3-CTB$^{2219}$ was dramatically reduced in psV lacking only the 2219 epitope and completely eliminated against psV lacking both the 2219 and 3074 epitopes (FIG. 6).

Together this data suggests that the engineered immunogen exclusively presenting the neutralization epitope targeted by the 3074 mAb—V3-CTB3074—elicited via immunization a neutralizing antibody response in rabbit serum that recapitulated the specificity of 3074. This response was distinct from that for V3-CTB2219, but both resulted in potent and broadly neutralizing animal sera as expected from the cross-strain distribution of their targeted epitopes. A small degree of cross-elicitation appears to have occurred between. Overall, close to half (9 of 19) Tier 1 and Tier 2 pseudoviruses from a published standard panel were neutralization-inhibited by the immune sera resulting from one or the other immunogen.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A recombinant immunogenic polypeptide comprising the amino acid sequence TESINIGPGQTFYA (SEQ ID NO:1).

2. The immunogenic polypeptide of claim 1, wherein the immunogenic polypeptide is in cyclized form.

3. An immunogenic pharmaceutical composition comprising:

the immunogenic polypeptide of claim 1 and an immunologically and pharmaceutically acceptable vehicle or excipient.

4. The immunogenic pharmaceutical composition of claim 3 further comprising:

an adjuvant or an immunostimulatory peptide or polypeptide that is different from said immunogenic polypeptide.

5. The immunogenic pharmaceutical composition of claim 4, wherein said immunostimulatory polypeptide is a cytokine.

6. The immunogenic pharmaceutical composition of claim 4, wherein the adjuvant is selected from the group consisting of: (a) ISAF-1 (5% squalene, 2.5% pluronic L121, 0.2% Tween 80) in phosphate-buffered solution with 0.4 mg of threonyl-muramyl dipeptide; (b) de-oiled lecithin dissolved in an oil; (c) aluminum hydroxide gel; (d) a mixture of (b) and (c); (e) QS-21; (f) monophosphoryl lipid A adjuvant; and (g) incomplete Freund's adjuvant.

7. A method for inducing a broadly neutralizing antibody response against a designed loop in a subject comprising:

selecting a subject and administering to the selected subject an effective amount of the immunogenic polypeptide according to claim 1 or the immunogenic pharmaceutical composition of claim 3.

8. The method of claim 7, wherein the selected subject is infected with HIV-1.

9. The method of claim 8, wherein the selected subject is infected with a form of HIV-1 heterologous to that from which the immunogenic polypeptide is derived.

10. The method of claim 7, wherein said administering is carried out intravenously, orally, transdermally, transmucosally, intrapleurally, intrathecally, by aerosol administration, or intraperitoneally.

11. A kit comprising in separate compartments in close proximity therein:

(a) one or more unit dosages of (i) the immunogenic polypeptide of claim 1, or (ii) the immunogenic pharmaceutical composition of claim 3, and (b) instructions for administering the immunogenic polypeptide or immunogenic pharmaceutical composition to a subject for inducing said broadly-neutralizing antibody response.

12. The immunogenic polypeptide of claim 1, wherein the loop peptide has the amino acid sequence TPQNITDLCA EYHNTQIHTL NDKIFSYTES LAGKREMAII TFCTRPSNNT TESINIGPGQ TFYATGEIIG DIRQAHCATF QVEVPGSQHI DSQKKAIERM KDTLRIAYLT EAKVEKLCVW NNKTPRAIAA ISMAN (SEQ ID NO:2).

* * * * *

SEQUENCE LISTING

```
<160> NUMBER OF SEQ ID NOS: 8

<210> SEQ ID NO 1
<211> LENGTH: 14
<212> TYPE: PRT
<213> ORGANISM: Artificial
<220> FEATURE:
<223> OTHER INFORMATION: V3 loop peptide insert

<400> SEQUENCE: 1

Thr Glu Ser Ile Asn Ile Gly Pro Gly Gln Thr Phe Tyr Ala
1               5                   10

<210> SEQ ID NO 2
<211> LENGTH: 135
<212> TYPE: PRT
<213> ORGANISM: Artificial
```

<220> FEATURE:
<223> OTHER INFORMATION: immunogenic polypeptide

<400> SEQUENCE: 2

Thr Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Cys Thr Arg Pro Ser Asn
        35                  40                  45

Asn Thr Thr Glu Ser Ile Asn Ile Gly Pro Gly Gln Thr Phe Tyr Ala
    50                  55                  60

Thr Gly Glu Ile Ile Gly Asp Ile Arg Gln Ala His Cys Ala Thr Phe
65                  70                  75                  80

Gln Val Glu Val Pro Gly Ser Gln His Ile Asp Ser Gln Lys Lys Ala
                85                  90                  95

Ile Glu Arg Met Lys Asp Thr Leu Arg Ile Ala Tyr Leu Thr Glu Ala
            100                 105                 110

Lys Val Glu Lys Leu Cys Val Trp Asn Asn Lys Thr Pro Arg Ala Ile
        115                 120                 125

Ala Ala Ile Ser Met Ala Asn
        130                 135

<210> SEQ ID NO 3
<211> LENGTH: 14
<212> TYPE: PRT
<213> ORGANISM: Artificial
<220> FEATURE:
<223> OTHER INFORMATION: V3 loop peptide insert

<400> SEQUENCE: 3

Arg Lys Ser Ile Asn Phe Gly Pro Gly Gln Thr Phe Tyr Ala
1               5                   10

<210> SEQ ID NO 4
<211> LENGTH: 135
<212> TYPE: PRT
<213> ORGANISM: Artificial
<220> FEATURE:
<223> OTHER INFORMATION: immunogenic polypeptide

<400> SEQUENCE: 4

Thr Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Cys Thr Arg Pro Ser Asn
        35                  40                  45

Asn Thr Arg Lys Ser Ile Asn Phe Gly Pro Gly Gln Thr Phe Tyr Ala
    50                  55                  60

Thr Gly Glu Ile Ile Gly Asp Ile Arg Gln Ala His Cys Ala Thr Phe
65                  70                  75                  80

Gln Val Glu Val Pro Gly Ser Gln His Ile Asp Ser Gln Lys Lys Ala
                85                  90                  95

Ile Glu Arg Met Lys Asp Thr Leu Arg Ile Ala Tyr Leu Thr Glu Ala
            100                 105                 110

Lys Val Glu Lys Leu Cys Val Trp Asn Asn Lys Thr Pro Arg Ala Ile
        115                 120                 125

```
Ala Ala Ile Ser Met Ala Asn
    130             135

<210> SEQ ID NO 5
<211> LENGTH: 124
<212> TYPE: PRT
<213> ORGANISM: Vibrio Cholerae

<400> SEQUENCE: 5

Met Ile Lys Leu Lys Phe Gly Val Phe Phe Thr Val Leu Leu Ser Ser
1               5                   10                  15

Ala Tyr Ala His Gly Thr Pro Gln Asn Ile Thr Asp Leu Cys Ala Glu
            20                  25                  30

Tyr His Asn Thr Gln Ile His Thr Leu Asn Asp Lys Ile Phe Ser Tyr
        35                  40                  45

Thr Glu Ser Leu Ala Gly Lys Arg Glu Met Ala Ile Ile Thr Phe Lys
    50                  55                  60

Asn Gly Ala Thr Phe Gln Val Glu Val Pro Gly Ser Gln His Ile Asp
65                  70                  75                  80

Ser Gln Lys Lys Ala Ile Glu Arg Met Lys Asp Thr Leu Arg Ile Ala
                85                  90                  95

Tyr Leu Thr Glu Ala Lys Val Glu Lys Leu Cys Val Trp Asn Asn Lys
            100                 105                 110

Thr Pro His Ala Ile Ala Ala Ile Ser Met Ala Asn
        115                 120

<210> SEQ ID NO 6
<211> LENGTH: 124
<212> TYPE: PRT
<213> ORGANISM: Escherichia coli

<400> SEQUENCE: 6

Met Asn Lys Val Lys Cys Tyr Val Leu Phe Thr Ala Leu Leu Ser Ser
1               5                   10                  15

Leu Cys Ala Tyr Gly Ala Pro Gln Ser Ile Thr Glu Leu Cys Ser Glu
            20                  25                  30

Tyr Arg Asn Thr Gln Ile Tyr Thr Ile Asn Asp Lys Ile Leu Ser Tyr
        35                  40                  45

Thr Glu Ser Met Ala Gly Lys Arg Glu Met Val Ile Ile Thr Phe Lys
    50                  55                  60

Ser Gly Ala Thr Phe Gln Val Glu Val Pro Gly Ser Gln His Ile Asp
65                  70                  75                  80

Ser Gln Lys Lys Ala Ile Glu Arg Met Lys Asp Thr Leu Arg Ile Thr
                85                  90                  95

Tyr Leu Thr Glu Thr Lys Ile Asp Lys Leu Cys Val Trp Asn Asn Lys
            100                 105                 110

Thr Pro Asn Ser Ile Ala Ala Ile Ser Met Glu Asn
        115                 120

<210> SEQ ID NO 7
<211> LENGTH: 35
<212> TYPE: PRT
<213> ORGANISM: Artificial
<220> FEATURE:
<223> OTHER INFORMATION: V3 loop peptide insert

<400> SEQUENCE: 7

Cys Thr Arg Pro Ser Asn Asn Thr Glu Ser Ile Asn Ile Gly Pro
1               5                   10                  15
```

-continued

```
Gly Gln Thr Phe Tyr Ala Thr Gly Glu Ile Ile Gly Asp Ile Arg Gln
            20                  25                  30

Ala His Cys
        35

<210> SEQ ID NO 8
<211> LENGTH: 35
<212> TYPE: PRT
<213> ORGANISM: Artificial
<220> FEATURE:
<223> OTHER INFORMATION: V3 loop peptide insert

<400> SEQUENCE: 8

Cys Thr Arg Pro Ser Asn Asn Thr Arg Lys Ser Ile His Ile Gly Pro
1               5                   10                  15

Gly Arg Ala Phe Tyr Thr Thr Gly Glu Ile Ile Gly Asp Ile Arg Gln
            20                  25                  30

Ala His Cys
        35
```

UNITED STATES PATENT AND TRADEMARK OFFICE
CERTIFICATE OF CORRECTION

PATENT NO. : 9,534,020 B2
APPLICATION NO. : 13/876918
DATED : January 3, 2017
INVENTOR(S) : Cardozo et al.

It is certified that error appears in the above-identified patent and that said Letters Patent is hereby corrected as shown below:

In the Specification

Column 1, at Line 13, add the following paragraph: --This invention was made with government support under grant number R01 AI084119 awarded by The National Institutes of Health. The government has certain rights in the invention.--

Signed and Sealed this
First Day of November, 2022

Katherine Kelly Vidal
*Director of the United States Patent and Trademark Office*